United States Patent
Felix et al.

(10) Patent No.: US 10,806,360 B2
(45) Date of Patent: Oct. 20, 2020

(54) EXTENDED WEAR AMBULATORY ELECTROCARDIOGRAPHY AND PHYSIOLOGICAL SENSOR MONITOR

(71) Applicant: Bardy Diagnostics, Inc., Seattle, WA (US)

(72) Inventors: Jason Felix, Vashon Island, WA (US); Gust H. Bardy, Carnation, WA (US); Jon Mikalson Bishay, Seattle, WA (US); Joshua Djon Green, Seattle, WA (US)

(73) Assignee: Bardy Diagnostics, Inc., Seattle, WA (US)

( * ) Notice: Subject to any disclaimer, the term of this patent is extended or adjusted under 35 U.S.C. 154(b) by 0 days.

(21) Appl. No.: 16/208,468

(22) Filed: Dec. 3, 2018

(65) Prior Publication Data

US 2019/0104961 A1   Apr. 11, 2019

Related U.S. Application Data

(63) Continuation-in-part of application No. 15/602,007, filed on May 22, 2017, now Pat. No. 10,398,334,
(Continued)

(51) Int. Cl.
*A61B 5/0408* (2006.01)
*A61B 5/0432* (2006.01)
(Continued)

(52) U.S. Cl.
CPC ........ *A61B 5/04087* (2013.01); *A61B 5/0006* (2013.01); *A61B 5/0022* (2013.01);
(Continued)

(58) Field of Classification Search
CPC .............. A61B 5/0408; A61B 5/04085; A61B 5/0432–04325; A61B 5/6832–6833;
(Continued)

(56) References Cited

U.S. PATENT DOCUMENTS 3,215,136 A   11/1965   Holter et al.
3,569,852 A   3/1971   Berkovits
(Continued)

FOREIGN PATENT DOCUMENTS

DE   19955211   5/2001
EP   1859833   11/2007
(Continued)

OTHER PUBLICATIONS 15 of The Hottest Wearable Gadgets, URL <http://thehottestgadgets.com/2008/09/the-15-hottest-wearable-gadgets-001253> (Web page cached on Sep. 27, 2008).
(Continued)

*Primary Examiner* — Lee S Cohen
*Assistant Examiner* — Erin M Cardinal
(74) *Attorney, Agent, or Firm* — Krista A. Wittman

(57) ABSTRACT

An extended wear electrocardiography patch is provided. A flexible backing includes an elongated strip of stretchable material. An electrocardiographic electrode is respectively affixed to and conductively exposed on each end of the elongated strip. A flexible circuit is affixed on each end to the elongated strip and includes a pair of circuit traces each originating within one of the ends of the elongated strip and coupled to one of the electrocardiographic electrodes. A non-conductive receptacle securely adhered on the one end of the elongated strip and includes electrode terminals aligned to interface the pair of circuit traces to an electrocardiography monitor to obtain electrocardiographic signals through the electrocardiographic electrodes. A crypto circuit includes memory programed with a sampling rate for at least one physiological sensor provided at least one of with the electrocardiography monitor and on the flexible backing to instruct the physiological sensor to obtain readings of physiological data.

20 Claims, 12 Drawing Sheets

Related U.S. Application Data which is a continuation of application No. 14/082,066, filed on Nov. 15, 2013, now Pat. No. 9,655,538, which is a continuation-in-part of application No. 14/080,717, filed on Nov. 14, 2013, now Pat. No. 9,545,204, and a continuation-in-part of application No. 14/080,725, filed on Nov. 14, 2013, now Pat. No. 9,730,593, application No. 16/208,468, which is a continuation-in-part of application No. 15/605,842, filed on May 25, 2017, which is a continuation-in-part of application No. 15/256,266, filed on Sep. 2, 2016, now Pat. No. 9,820,665, which is a continuation of application No. 14/082,071, filed on Nov. 15, 2013, now Pat. No. 9,433,367, which is a continuation-in-part of application No. 14/080,717, filed on Nov. 14, 2013, now Pat. No. 9,545,204, which is a continuation-in-part of application No. 14/080,725, filed on Nov. 14, 2013, now Pat. No. 9,730,593.

(60) Provisional application No. 61/882,403, filed on Sep. 25, 2013.

(51) Int. Cl.
| | | |
|---|---|---|
| *A61B 5/00* | (2006.01) | |
| *A61B 5/0402* | (2006.01) | |
| *G16H 50/20* | (2018.01) | |
| *A61B 5/021* | (2006.01) | |
| *A61B 5/087* | (2006.01) | |
| *A61B 5/145* | (2006.01) | |
| *A61B 5/01* | (2006.01) | |
| *A61B 5/08* | (2006.01) | |

(52) U.S. Cl.
CPC ........ *A61B 5/0402* (2013.01); *A61B 5/04085* (2013.01); *A61B 5/6823* (2013.01); *A61B 5/6833* (2013.01); *G16H 50/20* (2018.01); *A61B 5/01* (2013.01); *A61B 5/021* (2013.01); *A61B 5/04325* (2013.01); *A61B 5/087* (2013.01); *A61B 5/0816* (2013.01); *A61B 5/14532* (2013.01); *A61B 5/14542* (2013.01); *A61B 2560/045* (2013.01); *A61B 2562/08* (2013.01)

(58) Field of Classification Search
CPC .... A61B 2560/0408; A61B 2560/0412; A61B 2560/0443; A61B 2560/045; A61B 2560/0456; A61B 2560/0475; A61B 2562/0209; A61B 2562/08; A61B 2562/227

See application file for complete search history.

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,333,615 A | 8/1994 | Craelius et al. |
| 5,341,806 A | 8/1994 | Gadsby et al. |
| 5,348,008 A | 9/1994 | Bornn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,957,857 A | 9/1999 | Hartley |
| 5,984,102 A | 11/1999 | Tay |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,188,407 B1 | 2/2001 | Smith et al. |
| D443,063 S | 5/2001 | Pisani et al. |
| 6,245,025 B1 | 6/2001 | Torok et al. |
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 * | 10/2001 | Cordero ............ A61B 5/04085 600/372 |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |

(56) References Cited

U.S. PATENT DOCUMENTS

| | | |
|---|---|---|
| 6,454,708 B1 | 9/2002 | Ferguson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 * | 8/2003 | Del Mar ............ A61B 5/04085 600/507 |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bomzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Massif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,597,004 B2 | 3/2017 | Hughes et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 2002/0013538 A1 | 1/2002 | Teller |
| 2002/0013717 A1 | 1/2002 | Ando et al. |
| 2002/0016798 A1 | 2/2002 | Sakai |
| 2002/0103422 A1 | 8/2002 | Harder et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 | 3/2004 | Cao et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0207530 A1 | 10/2004 | Nielsen |
| 2004/0210165 A1 | 10/2004 | Marmaropoulos et al. |

(56) References Cited

U.S. PATENT DOCUMENTS

| | | |
|---|---|---|
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0096717 A1 | 5/2005 | Bishay et al. |
| 2005/0108055 A1 | 5/2005 | Ott et al. |
| 2005/0151640 A1 | 7/2005 | Hastings |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030904 A1 | 2/2006 | Quiles |
| 2006/0041201 A1 | 2/2006 | Behbehani et al. |
| 2006/0054737 A1 | 3/2006 | Richardson |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1* | 9/2007 | Kovacs ............... A61B 5/02055 600/300 |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0027339 A1 | 1/2008 | Nagai et al. |
| 2008/0051668 A1 | 2/2008 | Bardy |
| 2008/0058661 A1 | 3/2008 | Bardy |
| 2008/0143080 A1 | 3/2008 | Burr |
| 2008/0088467 A1* | 4/2008 | Al-Ali ............... A61B 5/14551 340/679 |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0177168 A1 | 7/2008 | Callahan et al. |
| 2008/0194927 A1 | 8/2008 | Kenknight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0312522 A1 | 12/2008 | Rowlandson et al. |
| 2009/0012412 A1 | 1/2009 | Wesel |
| 2009/0012979 A1 | 1/2009 | Bateni et al. |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1* | 3/2009 | Mazar ............... A61B 5/0402 600/300 |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1 | 5/2009 | Sims et al. |
| 2009/0156908 A1 | 6/2009 | Belalcazar et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1 | 1/2010 | Herleikson et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234715 A1 | 9/2010 | Shin et al. |
| 2010/0234716 A1 | 9/2010 | Engel |
| 2010/0280366 A1 | 11/2010 | Arne et al. |
| 2010/0312188 A1 | 12/2010 | Robertson et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0105861 A1 | 5/2011 | Derchak et al. |
| 2011/0144470 A1 | 6/2011 | Mazar et al. |
| 2011/0160548 A1 | 6/2011 | Forster |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kalb et al. |
| 2012/0003933 A1 | 1/2012 | Baker et al. |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |

(56) References Cited

U.S. PATENT DOCUMENTS

| | | |
|---|---|---|
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1* | 4/2012 | Boettcher .......... A61B 5/04001 600/384 |
| 2012/0101396 A1 | 4/2012 | Solosko et al. |
| 2012/0165645 A1 | 6/2012 | Russel et al. |
| 2012/0306662 A1 | 6/2012 | Vosch et al. |
| 2012/0172695 A1 | 7/2012 | Ko et al. |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0197380 A1 | 8/2013 | Oral et al. |
| 2013/0225963 A1 | 8/2013 | Kodandaramaiah et al. |
| 2013/0225966 A1 | 8/2013 | Macia Barber et al. |
| 2013/0231947 A1 | 9/2013 | Shusterman |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0012154 A1 | 1/2014 | Mazar et al. |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0140359 A1 | 5/2014 | Kalevo et al. |
| 2014/0180027 A1 | 6/2014 | Buller |
| 2014/0189928 A1 | 7/2014 | Oleson et al. |
| 2014/0206977 A1 | 7/2014 | Bahney et al. |
| 2014/0214134 A1 | 7/2014 | Peterson |
| 2014/0215246 A1 | 7/2014 | Lee et al. |
| 2014/0249852 A1 | 9/2014 | Proud |
| 2014/0296651 A1 | 10/2014 | Stone |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0048836 A1 | 2/2015 | Guthrie et al. |
| 2015/0065842 A1 | 3/2015 | Lee et al. |
| 2015/0094558 A1* | 4/2015 | Russell ................ A61B 5/6833 600/391 |
| 2015/0164349 A1 | 6/2015 | Gopalakrishnan et al. |
| 2015/0165211 A1 | 6/2015 | Naqvi et al. |
| 2015/0177175 A1 | 6/2015 | Elder et al. |
| 2015/0250422 A1* | 9/2015 | Bay ...................... A61B 5/6833 600/391 |
| 2015/0257670 A1 | 9/2015 | Ortega et al. |
| 2015/0305676 A1 | 11/2015 | Shoshani |
| 2015/0359489 A1 | 12/2015 | Baudenbacher et al. |
| 2016/0135746 A1 | 5/2016 | Kumar et al. |
| 2016/0144190 A1 | 5/2016 | Cao et al. |
| 2016/0144192 A1 | 5/2016 | Sanghera et al. |
| 2016/0217691 A1 | 7/2016 | Kadobayashi et al. |
| 2016/0235318 A1 | 8/2016 | Sarkar |
| 2017/0112399 A1 | 4/2017 | Brisben et al. |
| 2017/0156592 A1 | 6/2017 | Fu |
| 2017/0281032 A1 | 10/2017 | Weinberg et al. |
| 2017/0366921 A1 | 12/2017 | Pflugh et al. |
| 2018/0078771 A1 | 3/2018 | Koop et al. |
| 2019/0021671 A1 | 1/2019 | Kumar et al. |
| 2019/0059763 A1 | 2/2019 | Shakur et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | H11188015 | 7/1999 |
| JP | 2004129788 | 4/2004 |
| JP | 2007082938 | 4/2007 |
| JP | 2009219554 | 10/2009 |
| WO | 199852463 | 11/1998 |
| WO | 00/78213 | 12/2000 |
| WO | 2003032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 9/2010 |
| WO | 2011047207 | 4/2011 |
| WO | 2012140559 | 10/2012 |
| WO | 2012146957 | 11/2012 |
| WO | 2017072250 | 5/2017 |

OTHER PUBLICATIONS

Alivecor, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants At Neonatal Intensive Care Units Using Wearable Sensors," BodyNets 2010, Corfu Island, Greece. Sep. 10-12, 1210.

Epstein, Andrew E et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit Tracker, URL <http://www.fitbit.com/> (Web page cached on Sep. 10, 2008.).

Smith, Jawbone Up, URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid, "Technology Review, MIT. (May 1, 2009).

Lieberman, Jonathan, "How Telemedicine Is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013.).

Nike+ Fuel Band, URL <http://www.nike.com/us/en_us/c/nikeplus-fuelband> (Web page cached on Jan. 11, 2013.).

(56) References Cited

OTHER PUBLICATIONS

P. Libby et al.,"Braunwald's Heart Disease—A Textbook of Cardiovascular Medicine," Chs. 11, pp. 125-148 and 12, pp. 149-193 (8th ed. 2008), American Heart Association.
Initial hands-on with Polar Loop activity tracker, URL <http://www.dcrainmaker.com/2013/09/polar-loop-firstlook.html> (Sep. 17, 2013).
Seifert, Dan, Samsung dives into fitness wearable with the Gear Fit/ The Verge, URL <http://www.theverge.com/2014/2/24/5440310/samsung-dives-into-fitness-wearables-with-the-gear-fit> (Feb. 24, 2014).
Soper, Taylor, Samsung's new Galaxy S5 flagship phone has fingerprint reader, heart rate monitor, URL <http://www.geekwire.com/2014/samsung-galaxy-s5-fingerprint> (Feb. 24, 2014).
Dolcourt, See the Samsung Galaxy S5's Heart rate monitor in action, URL <http://www.cnet.com/news/see-the-samsung-galaxy-s5s-heart-rate-monitor-in-action> (Feb. 25, 2014).
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Sleepview, URL <http://www.clevemed.com/sleepview/overview.shtml> (Web page cached on Sep. 4, 2013.).
Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013.).
Zio Patch System, URL <http://www.irhythmtech.com/zio-solution/zio-system/index.html> (Web page cached on Sep. 8, 2013.).
Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.
Anonymous. "Omegawave Launches Consumer App 2.0 in U.S. Endurance Sportswire—Endurance Sportswire." Jul. 11, 2013. URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society.
Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.
Pranav Rajpurkar et al. "Cardiologist-Level Arrhythmia Detection with Convolutional Neural Networks," arxiv.org, Cornell University Library, 201 Olin Library Cornell University Ithaca, NY 14853, Jul. 6, 2017 (Jul. 6, 2017), XP080774895.
Pourbabaee Bahareh et al. "Feature Learning with Deep Convolutional Neural Networks for Screening Patients with Paroxysmal Atrial Fibrillation," 2016 Neural Networks (IJCNN), 2016 International Joint Conference on Neural Networks (IJCNN), IEEE, Jul. 24, 2016 (Jul. 24, 2016), pp. 5057-5064, XP032992832, DOI: 10.1109/IJCNN.2016.7727866.
Xiong Zhaohan et al. "Robust ECG Signal Classification for Detection of Atrial Fibrillation Using a Novel Neural Network," 2017 Computing in Cardiology (CinC), CCAL, Sep. 24, 2017 (Sep. 24, 2017), pp. 1-4, XP033343575, DOI: 10.22489/CinC.2017.066-138.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA-IEEE Medical Technology Conference on Individualized Healthcare. May 22, 2010.
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/j.1399-5618.2006.00364.x.
Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].
Vedapulse UK, Jan. 1, 2014 (Jan. 1, 2014), XP002757887, Retrieved from the Internet: URL:http://www.vedapulseuk.com/diagnostic/ [retrieved on May 19, 2016].
http://www.originlab.com/origin#Data_Exploration 2015.
https://web.archive.org/web/20130831204020/http://www.biopac.com/research.asp?CatID=37&Main=Software (Aug. 2013).
http://www.gtec.at/Products/Software/g.BSanalyze-Specs-Features (2014).
Adinstruments:ECG Analysis Module for LabChart & PowerLab, 2008.
BIOPAC Systems, Inc. #AS148-Automated ECG Analysis , Mar. 24, 2006.
Health Research—Hexoskin Biometric Shirt | Hexoskin URL:http://www.hexoskin.com/pages/health-research (Web page cached on Dec. 2, 2014).
Jacob Kastrenakes, "Apple Watch uses four sensors to detect your pulse," Sep. 9, 2014. URL: http://www.theverge.com/2014/9/9/6126991/apple-watch-four-back-sensors-detect-activity.
Nicole Lee, "Samsung Gear S review: an ambitious and painfully flawed smartwatch," Dec. 1, 2014. URL: http://www.engadget.com/2014/12/01/samsung-gear-s-review/.
G. G. Ivanov, "HRV Analysis Under the Usage of Different Electrocardiopraphy Systems," Apr. 15, 2008 (Apr. 15, 2008), XP55511209, Retrieved from the Internet: URL:http://www.drkucera.eu/upload_doc/hrv_analysis_(methodical_recommendations).pdf [retrieved on Oct. 1, 2018].

* cited by examiner

140

EXTENDED WEAR AMBULATORY ELECTROCARDIOGRAPHY AND PHYSIOLOGICAL SENSOR MONITOR

CROSS-REFERENCE TO RELATED APPLICATION

This non-provisional patent application is a continuation of U.S. Pat. No. 10,398,334, issued Sep. 3, 2019, which is a continuation of U.S. Pat. No. 9,655,538, issued May 23, 2017, which is a continuation-in-part of U.S. Pat. No. 9,545,204, issued Jan. 17, 2017, and is a continuation-in-part of U.S. Pat. No. 9,730,593, issued Aug. 15, 2017, and further claims priority under 35 U.S.C. § 119(e) to U.S. Provisional Patent application, Ser. No. 61/882,403, filed Sep. 25, 2013, the disclosures of which are incorporated by reference; this present non-provisional patent application is also a continuation of U.S. Pat. No. 10,433,748, issued Oct. 8, 2019, which is a continuation-in-part of U.S. Pat. No. 9,820,665, issued Nov. 21, 2017, which is a continuation of U.S. Pat. No. 9,433,367, issued Sep. 6, 2016, which is a continuation-in-part of U.S. Pat. No. 9,545,204, issued Jan. 17, 2017, and is a continuation-in-part of U.S. Pat. No. 9,730,593, issued Aug. 15, 2017, and further claims priority under 35 U.S.C. § 119(e) to U.S. Provisional Patent application, Ser. No. 61/882,403, filed Sep. 25, 2013, the disclosures of which are incorporated by reference.

FIELD

This application relates in general to electrocardiographic monitoring and, in particular, to an extended wear ambulatory electrocardiography and physiological sensor monitor.

BACKGROUND

The heart emits electrical signals as a by-product of the propagation of the action potentials that trigger depolarization of heart fibers. An electrocardiogram (ECG) measures and records such electrical potentials to visually depict the electrical activity of the heart over time. Conventionally, a standardized set format 12-lead configuration is used by an ECG machine to record cardiac electrical signals from well-established traditional chest locations. Electrodes at the end of each lead are placed on the skin over the anterior thoracic region of the patient's body to the lower right and to the lower left of the sternum, on the left anterior chest, and on the limbs. Sensed cardiac electrical activity is represented by PQRSTU waveforms that can be interpreted post-ECG recordation to derive heart rate and physiology. The P-wave represents atrial electrical activity. The QRSTU components represent ventricular electrical activity.

An ECG is a tool used by physicians to diagnose heart problems and other potential health concerns. An ECG is a snapshot of heart function, typically recorded over 12 seconds, that can help diagnose rate and regularity of heartbeats, effect of drugs or cardiac devices, including pacemakers and implantable cardioverter-defibrillators (ICDs), and whether a patient has heart disease. ECGs are used in-clinic during appointments, and, as a result, are limited to recording only those heart-related aspects present at the time of recording. Sporadic conditions that may not show up during a spot ECG recording require other means to diagnose them. These disorders include fainting or syncope; rhythm disorders, such as tachyarrhythmias and bradyarrhythmias; apneic episodes; and other cardiac and related disorders. Thus, an ECG only provides a partial picture and can be insufficient for complete patient diagnosis of many cardiac disorders.

Diagnostic efficacy can be improved, when appropriate, through the use of long-term extended ECG monitoring. Recording sufficient ECG and related physiology over an extended period is challenging, and often essential to enabling a physician to identify events of potential concern. A 30-day observation period is considered the "gold standard" of ECG monitoring, yet achieving a 30-day observation day period has proven unworkable because such ECG monitoring systems are arduous to employ, cumbersome to the patient, and excessively costly. Ambulatory monitoring in-clinic is implausible and impracticable. Nevertheless, if a patient's ECG could be recorded in an ambulatory setting, thereby allowing the patient to engage in activities of daily living, the chances of acquiring meaningful information and capturing an abnormal event while the patient is engaged in normal activities becomes more likely to be achieved.

For instance, the long-term wear of ECG electrodes is complicated by skin irritation and the inability ECG electrodes to maintain continual skin contact after a day or two. Moreover, time, dirt, moisture, and other environmental contaminants, as well as perspiration, skin oil, and dead skin cells from the patient's body, can get between an ECG electrode, the non-conductive adhesive used to adhere the ECG electrode, and the skin's surface. All of these factors adversely affect electrode adhesion and the quality of cardiac signal recordings. Furthermore, the physical movements of the patient and their clothing impart various compressional, tensile, and torsional forces on the contact point of an ECG electrode, especially over long recording times, and an inflexibly fastened ECG electrode will be prone to becoming dislodged. Notwithstanding the cause of electrode dislodgment, depending upon the type of ECG monitor employed, precise re-placement of a dislodged ECG electrode may be essential to ensuring signal capture at the same fidelity. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time; however, ensuring that the level of quality of ECG recording and patient service remains constant over an extended period of time is dependent upon the monitoring equipment being up to a known standard. Use of third party consumables, such as ECG electrodes, could undermine expectations of ECG recording fidelity and adversely skew monitoring results.

Conventionally, Holter monitors are widely used for long-term extended ECG monitoring. Typically, they are used for only 24-48 hours. A typical Holter monitor is a wearable and portable version of an ECG that include cables for each electrode placed on the skin and a separate battery-powered ECG recorder. The cable and electrode combination (or leads) are placed in the anterior thoracic region in a manner similar to what is done with an in-clinic standard ECG machine. The duration of a Holter monitoring recording depends on the sensing and storage capabilities of the monitor, as well as battery life. A "looping" Holter monitor (or event) can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest hinders or precludes a patient from replacing or removing the precordial leads and usually involves moving the patient from the physician office to a specialized center within the hospital or clinic.

The ZIO XT Patch and ZIO Event Card devices, manufactured by iRhythm Tech., Inc., San Francisco, Calif., are wearable stick-on monitoring devices that are typically worn on the upper left pectoral region to respectively provide continuous and looping ECG recording. The location is used to simulate surgically implanted monitors. Both of these devices are prescription-only and for single patient use. The ZIO XT Patch device is limited to a 14-day monitoring period, while the electrodes only of the ZIO Event Card device can be worn for up to 30 days. The ZIO XT Patch device combines both electronic recordation components, including battery, and physical electrodes into a unitary assembly that adheres to the patient's skin. The ZIO XT Patch device uses adhesive sufficiently strong to support the weight of both the monitor and the electrodes over an extended period of time and to resist disadherance from the patient's body, albeit at the cost of disallowing removal or relocation during the monitoring period. Moreover, throughout monitoring, the battery is continually depleted and battery capacity can potentially limit overall monitoring duration. The ZIO Event Card device is a form of downsized Holter monitor with a recorder component that must be removed temporarily during baths or other activities that could damage the non-waterproof electronics. Both devices represent compromises between length of wear and quality of ECG monitoring, especially with respect to ease of long term use, female-friendly fit, and quality of atrial (P-wave) signals. Moreover, both devices rely on the same set of ECG electrodes for the duration of the monitoring period; signal capture can suffer as the ECG electrodes disadhere from the patient's body over time.

Therefore, a need remains for an extended wear continuously recording ECG monitor practicably capable of being worn for a long period of time in both men and women and capable of recording atrial signals reliably with quality assurance implemented as part of disposable component replenishment.

A further need remains for a device capable of recording signals ideal for arrhythmia discrimination, especially a device designed for atrial activity recording.

SUMMARY

Physiological monitoring can be provided through a wearable monitor that includes two components, a flexible extended wear electrode patch and a removable reusable monitor recorder. The wearable monitor sits centrally (in the midline) on the patient's chest along the sternum oriented top-to-bottom. The placement of the wearable monitor in a location at the sternal midline (or immediately to either side of the sternum), with its unique narrow "hourglass"-like shape, benefits long-term extended wear by removing the requirement that ECG electrodes be continually placed in the same spots on the skin throughout the monitoring period. Instead, the patient is free to place an electrode patch anywhere within the general region of the sternum, the area most likely to record high quality atrial signals or P-waves. In addition, ensuring that the level of quality of ECG recording and patient service remains constant over an extended period of time is provided through self-authentication of electrode patches (and other accessories). The monitor recorder implements a challenge response scheme upon being connected to an electrode patch (or other accessory). Failing self-authentication, the monitor recorder signals an error condition. In addition, electrode patches (and other accessories) can be limited to operating for only a certain period of time, or with pre-defined operational parameters or privileges. In a further embodiment, a patient can purchase additional time, pre-defined operational parameters or privileges through a server-based subscription service.

One embodiment provides an extended wear electrocardiography and physiological sensor monitor recorder. A sealed housing is adapted to be removably secured into the non-conductive receptacle on a disposable extended wear electrode patch. Electronic circuitry is included within the sealed housing. An externally-powered micro-controller is operable to execute under micro programmable control only upon authentication of the disposable extended wear electrode patch during power up of the electronic circuitry. An electrocardiographic front end circuit is electrically interfaced to the micro-controller and is operable to sense electrocardiographic signals through electrocardiographic electrodes provided on the disposable extended wear electrode patch. Externally-powered flash memory is electrically interfaced with the micro-controller and is operable to store samples of the electrocardiographic signals.

A further embodiment provides an extended wear electrocardiography patch. A flexible backing includes an elongated strip of stretchable material. An electrocardiographic electrode is respectively affixed to and conductively exposed on each end of the elongated strip. A flexible circuit is affixed on each end to the elongated strip and includes a pair of circuit traces each originating within one of the ends of the elongated strip and coupled to one of the electrocardiographic electrodes. A non-conductive receptacle securely adhered on the one end of the elongated strip and includes electrode terminals aligned to interface the pair of circuit traces to an electrocardiography monitor to obtain electrocardiographic signals through the electrocardiographic electrodes. A crypto circuit includes memory programed with a sampling rate for at least one physiological sensor provided at least one of with the electrocardiography monitor and on the flexible backing to instruct the physiological sensor to obtain readings of physiological data.

A still further embodiment provides an extended wear electrocardiography and physiological sensor monitor. An electrocardiography monitor includes a sealed housing and electronic circuitry within the sealed housing, including an externally-powered micro-controller and an electrocardiographic front end circuit electrically interfaced to the micro-controller and operable to sense electrocardiographic signals. An electrocardiography patch includes a flexible backing formed of an elongated strip of stretchable material and an electrocardiographic electrode affixed to and conductively exposed on a contact surface of each end of the elongated strip. A flexible circuit is affixed on each end to the elongated strip and includes a pair of circuit traces each originating within one of the ends of the elongated strip and electrically coupled to one of the electrocardiographic electrodes. A non-conductive receptacle is securely adhered on the one end of the elongated strip opposite the contact surface and formed to removably receive the electrocardiography monitor. The non-conductive receptacle includes electrode terminals aligned to electrically interface the pair of circuit traces to the electrocardiography monitor. A crypto circuit includes memory programed with a sampling rate for at least one physiological sensor provided at least one of with the electrocardiography monitor and on the flexible backing to instruct the physiological sensor to obtain readings of physiological data.

The monitoring patch is especially suited to the female anatomy. The narrow longitudinal midsection can fit nicely within the intermammary cleft of the breasts without inducing discomfort, whereas conventional patch electrodes are wide and, if adhesed between the breasts, would cause chafing, irritation, frustration, and annoyance, leading to low patient compliance.

The foregoing aspects enhance ECG monitoring performance and quality, facilitating long-term ECG recording, critical to accurate arrhythmia diagnosis.

In addition, the foregoing aspects enhance comfort in women (and certain men), but not irritation of the breasts, by placing the monitoring patch in the best location possible for optimizing the recording of cardiac signals from the atrium, another feature critical to proper arrhythmia diagnosis.

Finally, the foregoing aspects as relevant to monitoring are equally applicable to recording other physiological measures, such as temperature, respiratory rate, blood sugar, oxygen saturation, and blood pressure, as well as other measures of body chemistry and physiology.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
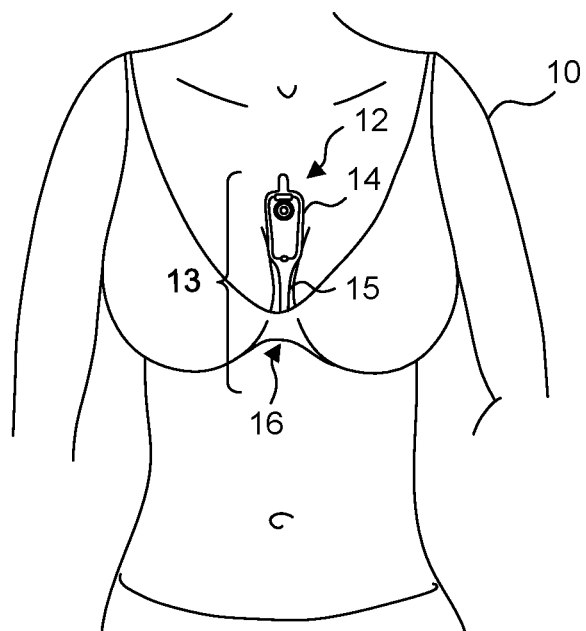
FIGS. 1 and 2 are diagrams showing, by way of examples, an extended wear electrocardiography and physiological sensor monitor respectively fitted to the sternal region of a female patient and a male patient.
Figure 2:
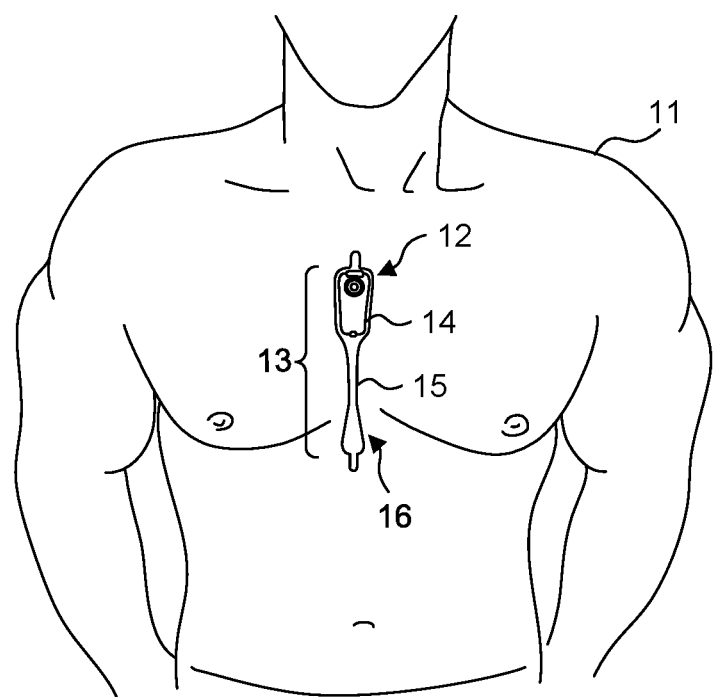

Physiological monitoring can be provided through a wearable monitor that includes two components, a flexible extended wear electrode patch and a removable reusable monitor recorder. FIGS. 1 and 2 are diagrams showing, by way of examples, an extended wear electrocardiography and physiological sensor monitor 12, including a monitor recorder 14 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. In a further embodiment, the orientation of the wearable monitor 12 can be corrected post-monitoring, as further described infra. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity, while simultaneously facilitating comfortable long-term wear for many weeks. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region or lateral thoracic region or the limb leads. In addition, placing the lower or inferior pole (ECG electrode) of the electrode patch 15 over (or near) the Xiphoid process facilitates sensing of ventricular activity and provides superior recordation of the QRS interval.

Figure 3:
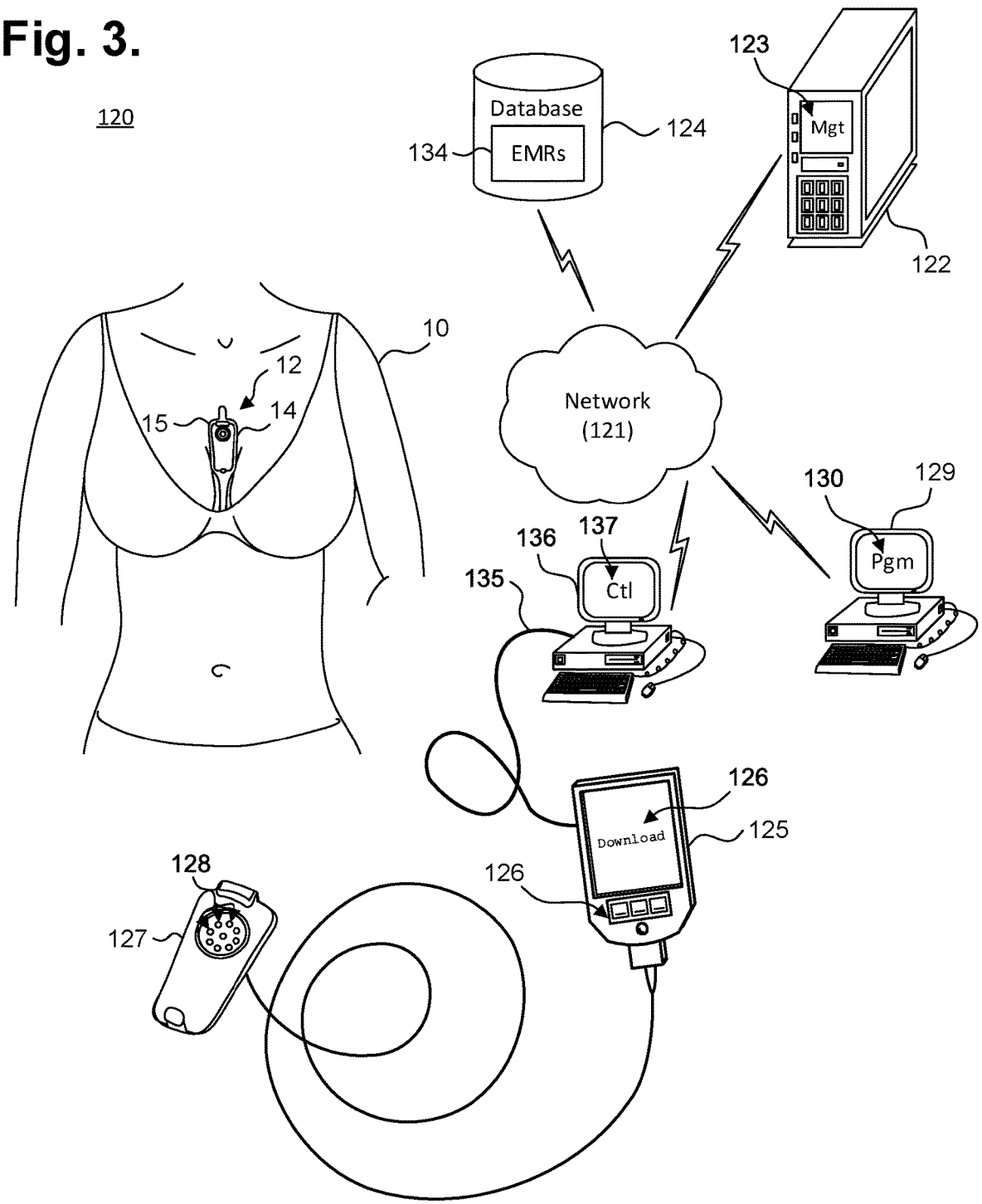
FIG. 3 is a functional block diagram showing a system for providing a self-authenticating electrocardiography monitoring circuit in accordance with one embodiment.

The monitor recorder 14 of the extended wear electrocardiography and physiological sensor monitor 12 senses and records the patient's ECG data into an onboard memory. Over time, disposable electrode patches 15 will require replacement and ensuring that the level of quality of ECG recording and patient service remains constant over an extended period of time is dependent upon the monitoring equipment, particularly the replacement electrode patches 15, being up to a known standard. FIG. 3 is a functional block diagram showing a system 120 for providing a self-authenticating electrocardiography monitoring circuit in accordance with one embodiment. Self-authentication allows quality and safety expectations to be maintained. The monitor recorder 14 is a reusable component that can be fitted during patient monitoring into a non-conductive receptacle provided on the electrode patch 15, as further described infra with reference to FIG. 4, and later removed for offloading of stored ECG data or to receive revised programming. The monitor recorder 14 executes an authentication protocol as part of a power up sequence, as further described infra with reference to FIG. 11. Following completion of ECG monitoring, the monitor recorder 14 can be connected to a download station 125, which could be a programmer or other device that permits the retrieval of stored ECG monitoring data, execution of diagnostics on or programming of the monitor recorder 14, or performance of other functions. The monitor recorder 14 has a set of electrical contacts (not shown) that enable the monitor recorder 14 to physically interface to a set of terminals 128 on a paired receptacle 127 of the download station 125. In turn, the download station 125 executes a communications or offload program 126 ("Offload") or similar program that interacts with the monitor recorder 14 via the physical interface to retrieve the stored ECG monitoring data. The download station 125 could be a server, personal computer, tablet or handheld computer, smart mobile device, or purpose-built programmer designed specific to the task of interfacing with a monitor recorder 14. Still other forms of download station 125 are possible.

Upon retrieving stored ECG monitoring data from a monitor recorder 14, middleware first operates on the retrieved data to adjust the ECG waveform, as necessary, and to convert the retrieved data into a format suitable for use by third party post-monitoring analysis software. The formatted data can then be retrieved from the download station 125 over a hard link 135 using a control program 137 ("Ctl") or analogous application executing on a personal computer 136 or other connectable computing device, via a communications link (not shown), whether wired or wireless, or by physical transfer of storage media (not shown). The personal computer 136 or other connectable device may also execute middleware that converts ECG data and other information into a format suitable for use by a third-party post-monitoring analysis program, as further described infra with reference to FIG. 13. Note that formatted data stored on the personal computer 136 would have to be maintained and safeguarded in the same manner as electronic medical records (EMRs) 134 in the secure database 124, as further discussed infra. In a further embodiment, the download station 125 is able to directly interface with other devices over a computer communications network 121, which could be some combination of a local area network and a wide area network, including the Internet, over a wired or wireless connection.

A client-server model could be used to employ a server 122 to remotely interface with the download station 125 over the network 121 and retrieve the formatted data or other information. The server 122 executes a patient management program 123 ("Mgt") or similar application that stores the retrieved formatted data and other information in a secure database 124 cataloged in that patient's EMRs 134. In addition, the patient management program 123 could manage a subscription service that authorizes a monitor recorder 14 to operate for a set period of time or under pre-defined operational parameters and privileges, such as described in infra with reference to FIG. 13.

The patient management program 123, or other trusted application, also maintains and safeguards the secure database 124 to limit access to patient EMRs 134 to only authorized parties for appropriate medical or other uses, such as mandated by state or federal law, such as under the Health Insurance Portability and Accountability Act (HIPAA) or per the European Union's Data Protection Directive. For example, a physician may seek to review and evaluate his patient's ECG monitoring data, as securely stored in the secure database 124. The physician would execute an application program 130 ("Pgm"), such as a post-monitoring ECG analysis program, on a personal computer 129 or other connectable computing device, and, through the application 130, coordinate access to his patient's EMRs 134 with the patient management program 123. Other schemes and safeguards to protect and maintain the integrity of patient EMRs 134 are possible.

Figure 4:
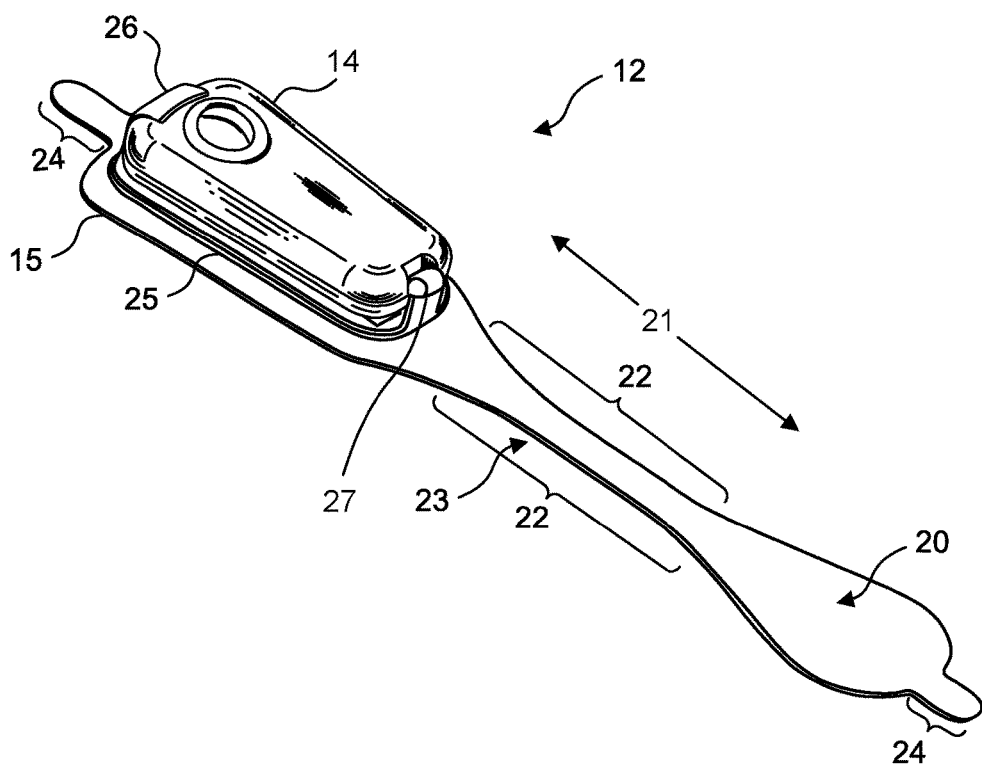
FIG. 4 is a perspective view showing an extended wear electrode patch with a monitor recorder in accordance with one embodiment inserted.

During use, the electrode patch 15 is first adhesed to the skin along the sternal midline 16 (or immediately to either side of the sternum 13). A monitor recorder 14 is then snapped into place on the electrode patch 15 to initiate ECG monitoring. FIG. 4 is a perspective view showing an extended wear electrode patch 15 with a monitor recorder 14 in accordance with one embodiment inserted. The body of the electrode patch 15 is preferably constructed using a flexible backing 20 formed as an elongated strip 21 of wrap knit or similar stretchable material with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above.

The electrode patch 15 incorporates features that significantly improve wearability, performance, and patient comfort throughout an extended monitoring period. During wear, the electrode patch 15 is susceptible to pushing, pulling, and torqueing movements, including compressional and torsional forces when the patient bends forward, and tensile and torsional forces when the patient leans backwards. To counter these stress forces, the electrode patch 15 incorporates strain and crimp reliefs, such as described in commonly-assigned U.S. Pat. No. 9,545,204, issued Jan. 17, 2017, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, such as described in commonly-assigned U.S. Pat. No. 9,720,593, issued Aug. 15, 2017, the disclosure of which is incorporated by reference. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 5:
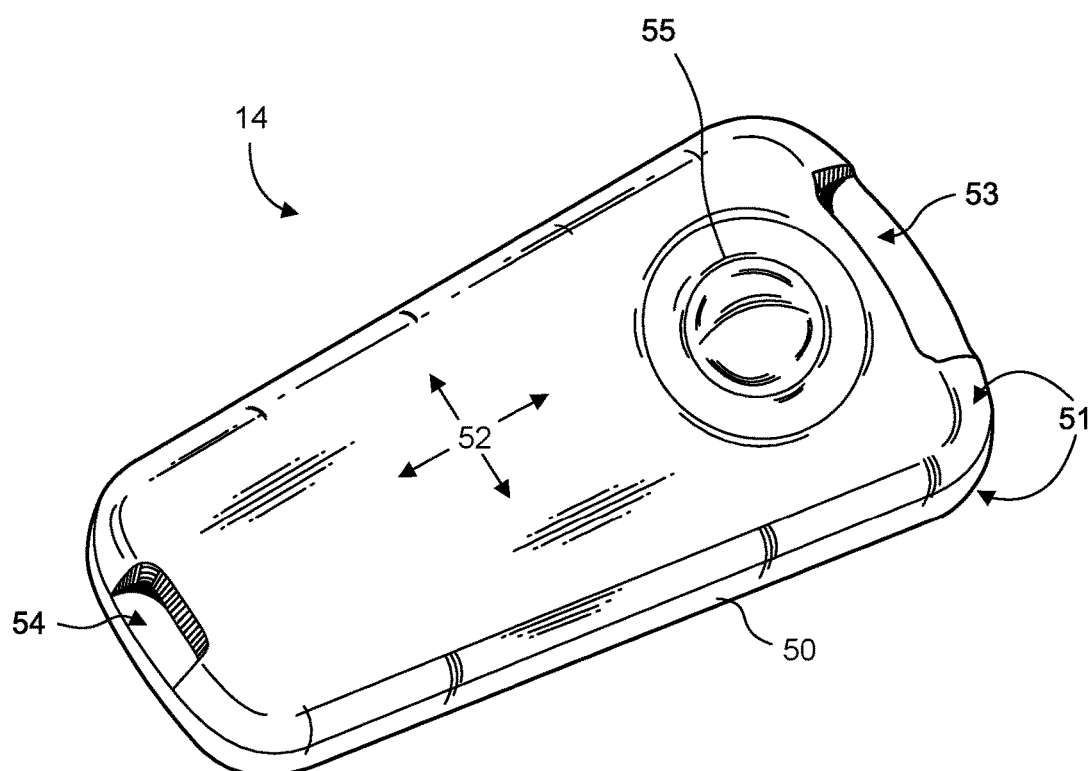
FIG. 5 is a perspective view showing the monitor recorder of FIG. 4.

The monitor recorder 14 includes a sealed housing that snaps into place in the non-conductive receptacle 25. FIG. 5 is a perspective view showing the monitor recorder 14 of FIG. 4. The sealed housing 50 of the monitor recorder 14 intentionally has a rounded isosceles trapezoidal-like shape 52, when viewed from above, such as described in commonly-assigned U.S. Design Pat. No. D717955, issued Nov. 18, 2014, the disclosure of which is incorporated by reference. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 6:
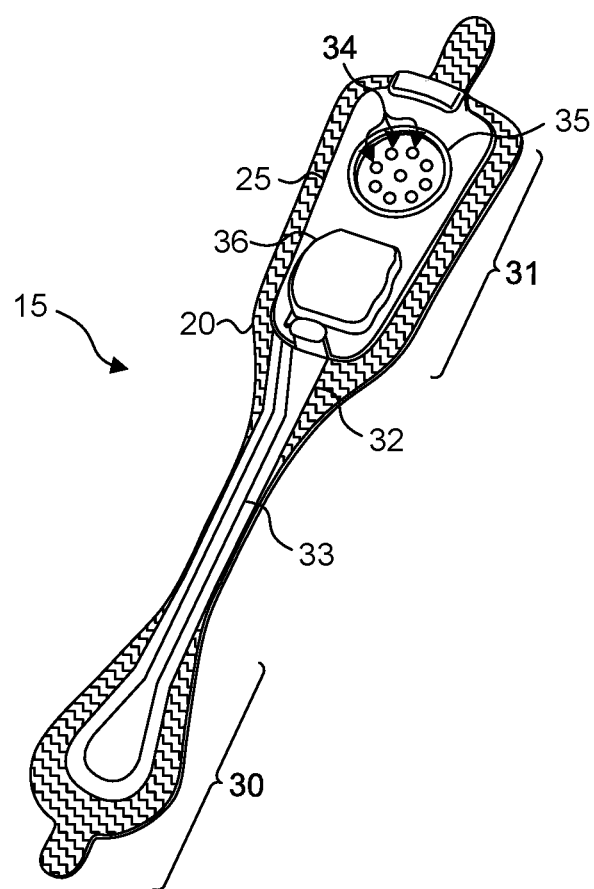
FIG. 6 is a perspective view showing the extended wear electrode patch of FIG. 4 without a monitor recorder inserted.

During use, the electrode patch 15 is first adhered to the skin in the sternal region. FIG. 6 is a perspective view showing the extended wear electrode patch 15 of FIG. 4 without a monitor recorder 14 inserted. A flexible circuit 32 is adhered to each end of the flexible backing 20. A distal circuit trace 33 and a proximal circuit trace (not shown) electrically couple ECG electrodes (not shown) to a pair of electrical pads 34. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14, and the moisture-resistant seal 35 enables the monitor recorder 14 to be worn at all times, even during bathing or other activities that could expose the monitor recorder 14 to moisture.

In addition, a battery compartment 36 is formed on the bottom surface of the non-conductive receptacle 25, and a pair of battery leads (not shown) electrically interface the battery to another pair of the electrical pads 34. The battery contained within the battery compartment 35 can be replaceable, rechargeable or disposable.

Figure 7:
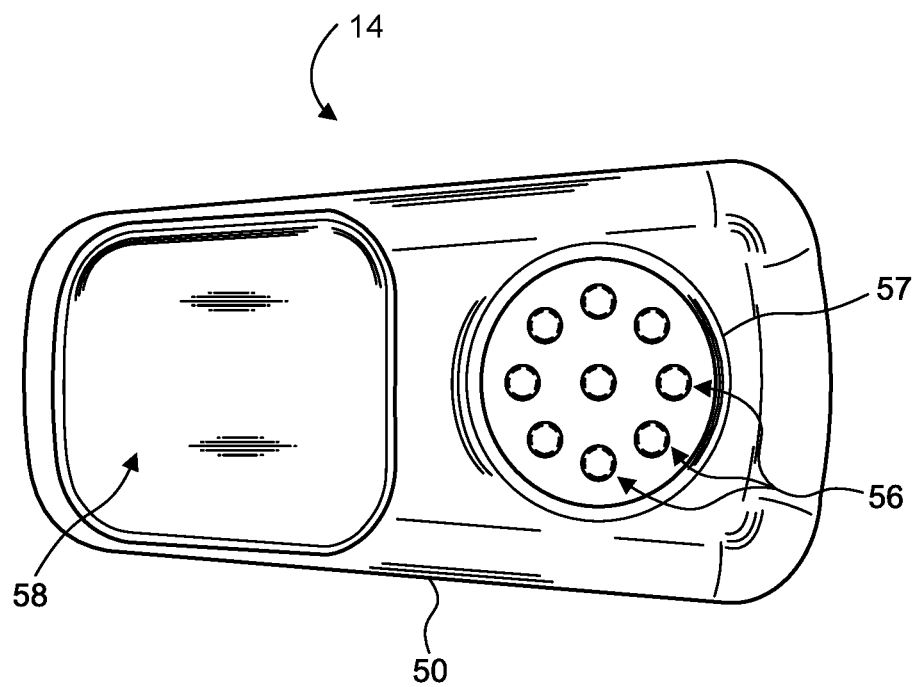
FIG. 7 is a bottom plan view of the monitor recorder of FIG. 4.

The monitor recorder 14 draws power externally from the battery provided in the non-conductive receptacle 25, thereby uniquely obviating the need for the monitor recorder 14 to carry a dedicated power source. FIG. 7 is a bottom plan view of the monitor recorder 14 of FIG. 4. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 8:
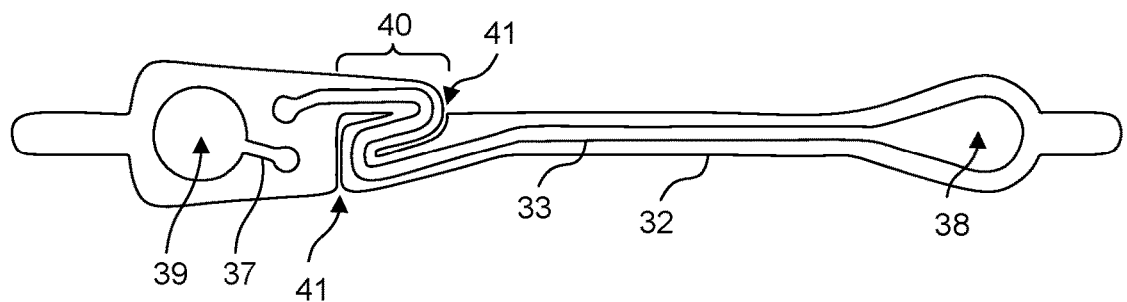
FIG. 8 is a top view showing the flexible circuit of the extended wear electrode patch of FIG. 4 when mounted above the flexible backing.

Unlike the flexible backing 20, the flexible circuit 32 is only able to bend and cannot stretch in a planar direction. The flexible circuit 32 can be provided either above or below the flexible backing 20. FIG. 8 is a top view showing the flexible circuit 32 of the extended wear electrode patch 15 of FIG. 4 when mounted above the flexible backing 20. A distal ECG electrode 38 and proximal ECG electrode 39 are respectively coupled to the distal and proximal ends of the flexible circuit 32. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 9:
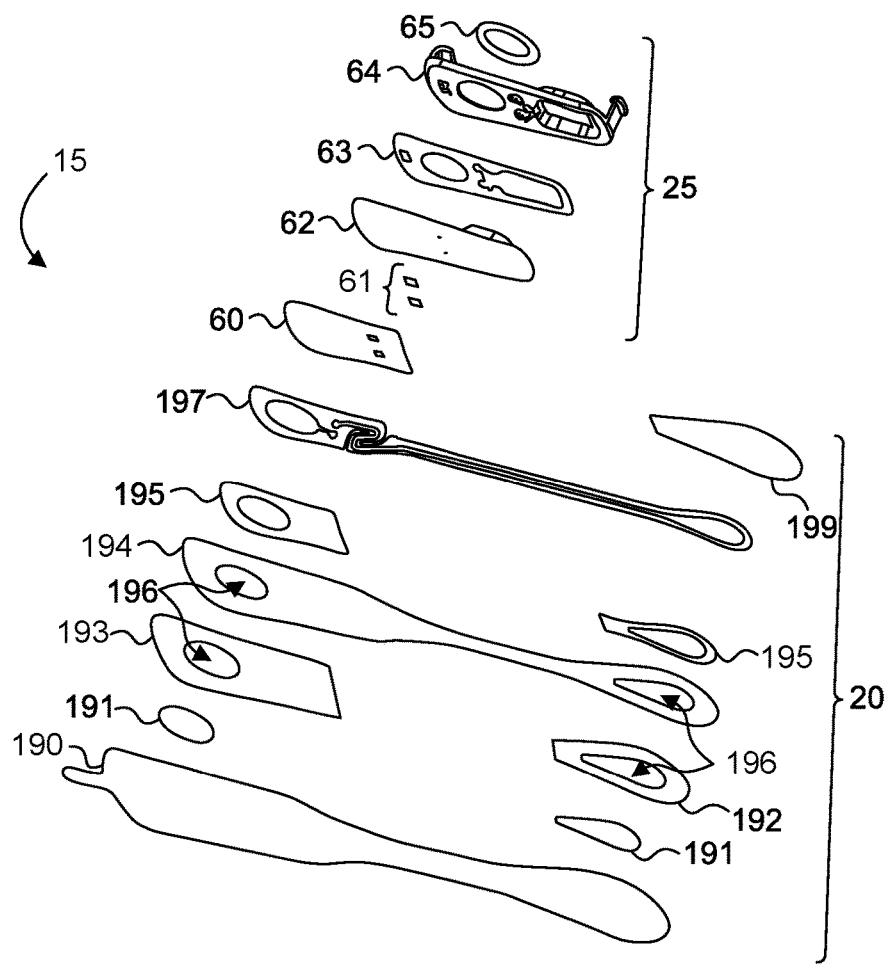
FIG. 9 is an exploded view showing the component layers of the extended wear electrode patch of FIG. 4.

When provided above the flexible backing 20, adhesive layers are provided above and below the flexible circuit 32. FIG. 9 is an exploded view showing the component layers of the electrode patch 15 of FIG. 4. The flexible backing 20 is constructed of a wearable gauze, latex, or similar wrap knit or stretchable and wear-safe material 54, such as a Tricot-type linen with a pressure sensitive adhesive (PSA) on the underside, or contact, surface. The wearable material 194 is coated with a layer 193, 192 of non-irritating adhesive, such as hydrocolloid, to facilitate long-term wear. The hydrocolloid, for instance, is typically made of mineral oil, cellulose and water and lacks any chemical solvents, so should cause little itching or irritation. Moreover, hydrocolloid is thicker and more gel-like than most forms of PSA and provides cushioning between the relatively rigid and unyielding non-conductive receptacle 25 and the patient's skin. In a further embodiment, the layer of non-irritating adhesive can be contoured, such as by forming the adhesive with a concave or convex cross-section; surfaced, such as through stripes or crosshatches of adhesive, or by forming dimples in the adhesive's surface; or applied discontinuously, such as with a formation of discrete dots of adhesive.

As described supra with reference to FIG. 8, a flexible circuit can be adhered to either the outward facing surface or the underside, or contact, surface of the flexible backing 20. For convenience, a flexible circuit 197 is shown, such as in FIG. 9, relative to the outward facing surface of the wearable material 194 and is adhered respectively on a distal end by a distal electrode seal 195 and on a proximal end by a proximal electrode seal 195. In a further embodiment, the flexible circuit 197 can be provided on the underside, or contact, surface of the wearable material 194. Through the electrode seals, only the distal and proximal ends of the flexible circuit 197 are attached to the wearable material 194, which enables the strain relief 50 (shown in FIG. 8) to respectively longitudinally extend and twist in response to tensile and torsional forces during wear. Similarly, the layer 193, 192 of non-irritating adhesive is provided on the underside, or contact, surface of the wearable material 194 only on the proximal and distal ends, which enables the longitudinal midsection 23 (shown in FIG. 4) to respectively bow outward and away from the sternum 13 or twist in response to compressional and torsional forces during wear. In a further embodiment, the layer 193, 192 of non-irritating adhesive is provided along a length of the wearable material 194.

A pair of openings 196 is defined on the distal and proximal ends of the wearable material 194 and layer 193, 192 of non-irritating adhesive for ECG electrodes 38, 39 (shown in FIG. 8). The openings 196 serve as "gel" wells with a layer of hydrogel 191 being used to fill the bottom of each opening 196 as a conductive material that aids electrode signal pick up. The entire underside, or contact, surface of the flexible backing 20 is protected prior to use by a liner layer 190 that is peeled away.

The non-conductive receptacle 25 includes a main body 64 that is molded out of polycarbonate, ABS, or an alloy of those two materials to provide a high surface energy to facilitate adhesion of an adhesive seal 63. The main body 64 is attached to a battery printed circuit board 62 by the adhesive seal 63 and, in turn, the battery printed circuit board 62 is adhesed to the flexible circuit 197 with an upper flexible circuit seal 60. A pair of conductive transfer adhesive points 61 or, alternatively, metallic rivets or similar conductive and structurally unifying components, connect the circuit traces 33, 37 (shown in FIG. 8) of the flexible circuit 197 to the battery printed circuit board 62. The main body 64 has a retention catch 26 and tension clip 27 (shown in FIG. 4) that fixably and securely receive a monitor recorder 14 (shown in FIG. 4), and includes a recess within which to circumferentially receive a die cut gasket 65, either rubber, urethane foam, or similar suitable material, to provide a moisture resistant seal to the set of pads 34 (shown in FIG. 6).

Figure 10:
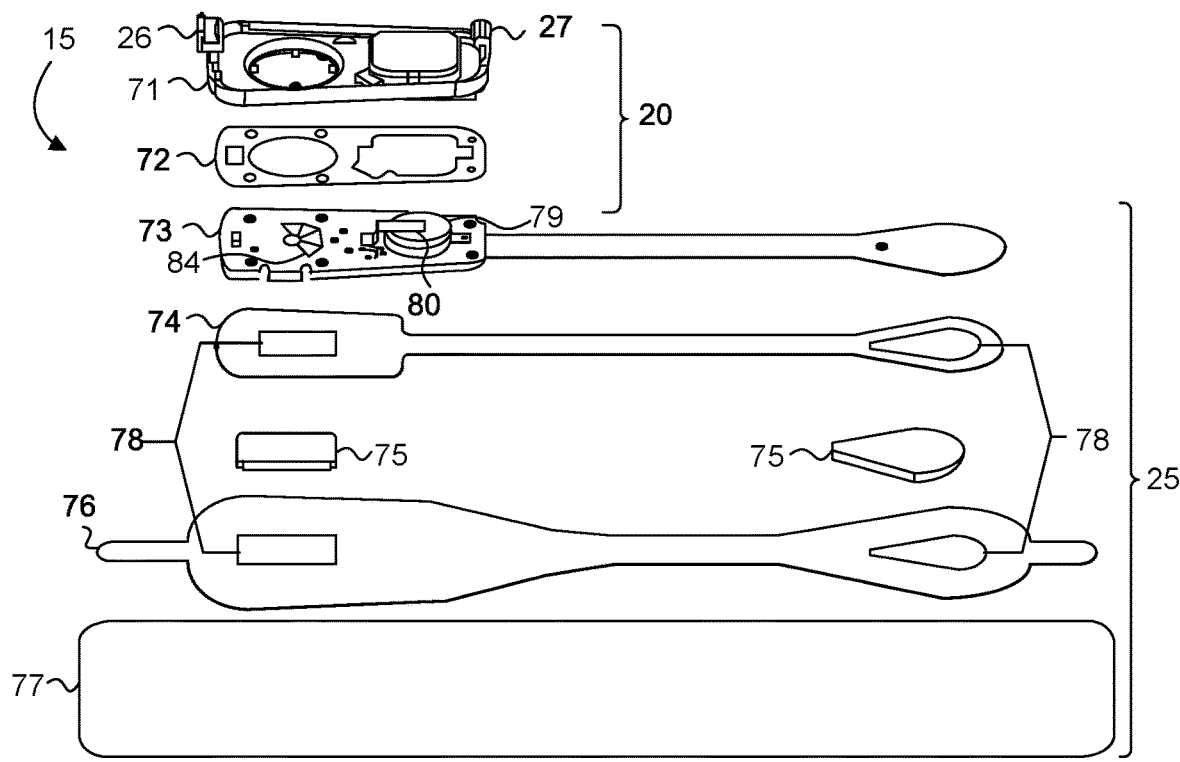
FIG. 10 is an alternative exploded view showing the component layers of the extended wear electrode patch of FIG. 4.

Together, the components of the electrode patch 15, as described above, form a signal path for transmission of ECG data sensed by the electrodes, to the recorder monitor for collection and transfer to a download station. Reducing a number of components in the signal path can simplify fabrication and decrease manufacturing costs, as well as enhance noise reduction. FIG. 10 is an alternative exploded view showing the component layers of the electrode patch 15 of FIG. 4. The non-conductive receptacle 20 is provided on a top surface of the flexible backing 25 to conformably receive and securely hold the monitor recorder 14 (shown in FIG. 4) in place. The flexible backing 25 can include an integrated flex circuit 73, electrode seal 74, patient adhesive 76, and a liner layer 77. The flexible backing can also include ECG electrodes (not shown) and hydrogel 75, which is in contact with the ECG electrodes.

The integrated flex circuit 73 can be constructed from material, such as polyester substrate and silver ink, and can include a pair of circuit traces (not shown), one on a distal end and one on a proximal end of the integrated flex circuit. The circuit traces electrically couple the ECG electrodes to a pair of electrical pads 84 on the integrated flex circuit. Specifically, the silver ink is applied to the polyester substrate of the integrated flex circuit 73 for electrical conductivity of the circuit traces (shown in FIG. 8) using screen-printing, pad-printing, or flexography. Other types of material, ink and means for electrical conductivity are possible. Two or more of the electrical pads are formed on the outward facing surface of the integrated flex circuit, which can also form a bottom surface of the non-conductive receptacle 20. Additionally, one or more electrical pads can also be located on a contact surface of the integrated flexible circuit.

A battery 79 is adhered directly to the outward facing surface of the integrated flex circuit 73, removing the need for a battery printed circuit board, adhesive points and a flexible circuit seal, as shown in FIG. 9, which is described above in detail. The battery 79 can be soldered to the integrated flex circuit 73 or alternatively, the battery 79 is affixed to the integrated flex circuit 73 via a clip 80. Other means for attaching the battery 79 to the integrated flex circuit 73 are possible.

A layer of patient adhesive 76 is provided on the contact surface of the integrated flex circuit 73 via one or more electrode seals 74. The electrode seal 74 includes a double sided layer of adhesive to connect the integrated flex circuit 73 and the adhesive layer 76. The adhesive layer 76 is a type of wearable material coated on a bottom, or contact, surface with a layer of non-irritating adhesive, such as hydrocolloid. The wearable material can include gauze, latex, wrap knit, or other types of stretchable and wear-safe material, such as a Tricot-type linen with a pressure sensitive adhesive on the underside, or contact surface. The electrode seal 74 and adhesive layer 76 can each cover the entire contact surface of the integrated flex circuit 73 or merely a portion, such as on proximal and distal ends of the integrated flex circuit 73.

Further, openings 78 are defined on the distal and proximal ends of each of the electrode seal 74 and adhesive layer 76 for ECG electrodes 38, 39 (shown in FIG. 8). The openings serve as "gel" wells with a layer of hydrogel 75 used to fill the bottom of each opening as a conductive material that aids signal pick up by the electrodes, which are electrically coupled to the circuit traces. The entire underside, or contact, surface of the flexible backing 20 is protected prior to use by a liner layer 77 that is peeled away.

The non-conductive receptacle 20 includes a main body 71 that is molded out of polycarbonate, ABS, or an alloy of those two materials to provide a high surface energy to facilitate adhesion of an adhesive seal 72. The main body 71 is adhesed to the integrated flex circuit 73 via the adhesive seal 72 and has a retention catch 26 and tension clip 27 (shown in FIG. 4) that fixably and securely receive a monitor recorder 14 (not shown). The main body 71 also includes a recess within which to circumferentially receive a die cut gasket (not shown), either rubber, urethane foam, or similar suitable material, to provide a moisture resistant seal to the set of pads 34 (shown in FIG. 6).

Figure 11:
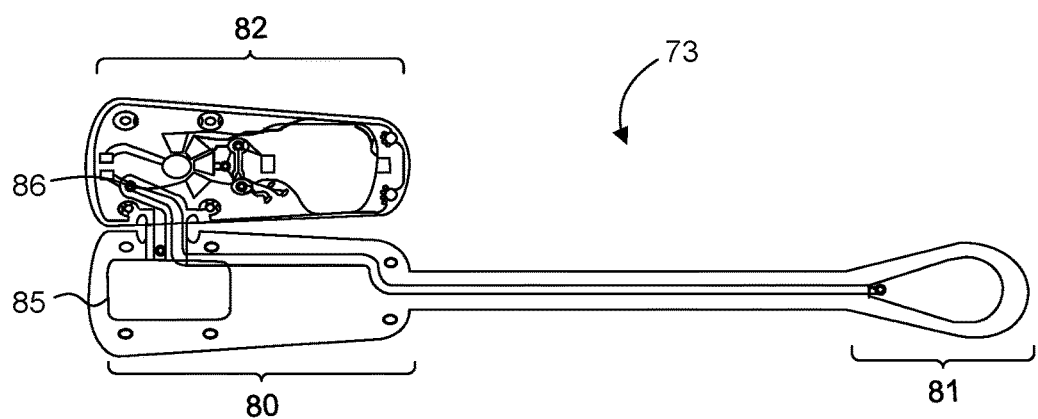
FIG. 11 is an exploded view showing an integrated flex circuit of the extended wear electrode patch of FIG. 10.

Decreasing a number of components in the electrode patch can help decrease noise in the collection of ECG data from a patient, which is extremely important because some types of noise can look like certain kinds of arrythmias. The integrated flex circuit includes a battery, removing the need for a separate printed circuit board. FIG. 11 is an exploded view showing the integrated flex circuit 73 of the electrode patch of FIG. 10. The integrated flex circuit 73 is formed from a single piece of material, such as polyester substrate. As described above with respect to FIG. 4, a pair of cut-outs between distal and proximal ends of the electrode patch create a narrow longitudinal midsection and defines an elongated "hourglass"-like shape of the integrated flex circuit, in one embodiment. The integrated flex circuit 73 can also be shaped in the elongated "hourglass"-like shape, consistent with the electrode patch. Further, an upper portion 80 of the "hourglass" shaped integrated flex circuit is formed on proximal end and sized to hold the electrically non-conductive receptacle (not shown). The upper 80 portion has a longer and wider profile than the lower part 81 of the "hourglass," which is sized primarily to allow just the placement of an ECG electrode. Additionally, the integrated flex circuit 73 includes a duplicate 82 of the upper portion 80 that is a mirror image and connected to the upper portion along one side. The mirror copy 82 of the upper portion is folded over the upper portion 80. Other shapes of the electrode patch and the integrated flex circuit are possible, including rectangular, square, oval, and circular.

Each of the upper portion and the mirror copy of the upper portion can include electrical pads 85, 86, which establish electrical connections between the electrode patch and the monitor recorder. Specifically, the electrical pads on the mirror copy of the upper portion interface to electrical contacts (not shown) protruding from the bottom surface of the monitor recorder.

In a further embodiment, one or both of the electrode patch 15 and integrated flex circuit 73 form a different shape, such as a long rectangular strip or another shape. In such configuration, a portion of the integrated flex circuit 73 is designated as the upper portion and duplicated to form a mirror image, which is folded over the designed upper portion.

Due to the flexible nature of the integrated circuit, a stiffener is used to prevent unnecessary bending of the circuit, such as when a patient presses a tactile feedback button on the monitor to mark events or to perform other functions. In one embodiment, the stiffener can be the same shape and size as the integrated flex circuit and can be made from epoxy laminate sheets or fiberglass. In another embodiment, the upper portion is folded over a stiffener, which is located between the upper portion and the mirror copy, and laminated together.

Figure 12:
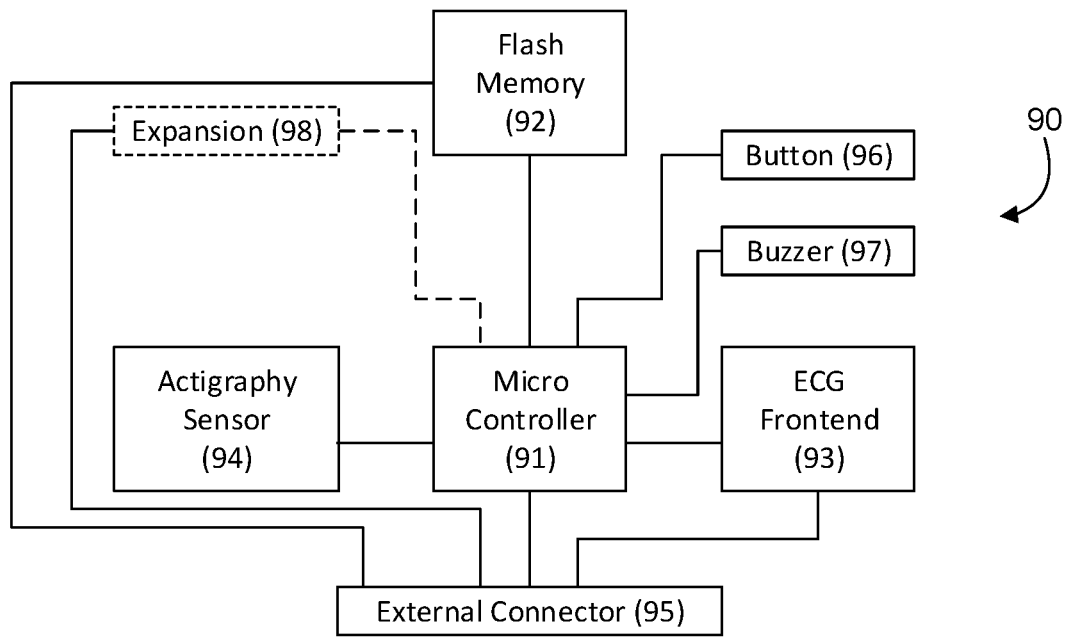
FIG. 12 is a functional block diagram showing the component architecture of the circuitry of the monitor recorder of FIG. 4.

When inserted in the non-conductive receptacle of the electrode patch, the monitor recorder performs ECG monitoring and other functions through a micro controlled architecture. FIG. 12 is a functional block diagram showing the component architecture of the circuitry 90 of the monitor recorder 14 of FIG. 4. The circuitry 90 is externally powered through a battery provided in the non-conductive receptacle 25 (shown in FIG. 6). Both power and raw ECG signals, which originate in the pair of ECG electrodes 38, 39 (shown in FIG. 8) on the distal and proximal ends of the electrode patch 15, are received through an external connector 95 that mates with a corresponding physical connector on the electrode patch 15. The external connector 95 includes the set of electrical contacts 56 (shown in FIG. 7) that protrude from the bottom surface of the sealed housing 50 and which physically and electrically interface with the set of pads 34 (shown in FIG. 6) provided on the bottom surface of the non-conductive receptacle 25. The external connector 95 includes electrical contacts 56 for data download, microcontroller communications, power, analog inputs, and a peripheral expansion port. The arrangement of the pins on the external connector 95 of the monitor recorder 14 and the device into which the monitor recorder 14 is attached, whether an electrode patch 15 or download station 125 (shown in FIG. 3), follow the same electrical pin assignment convention to facilitate interoperability. The external connector 65 also serves as a physical interface to a download station that permits the retrieval of stored ECG monitoring data, communication with the monitor recorder 14, and performance of other functions.

Operation of the circuitry 90 of the monitor recorder 14 is managed by a microcontroller 91. The micro-controller 91 includes a program memory unit containing internal flash memory that is readable and writeable. The internal flash memory can also be programmed externally. The micro-controller 91 draws power externally from the battery provided on the electrode patch 15 via a pair of the electrical contacts 56. The microcontroller 91 connects to the ECG front end circuit 93 that measures raw cutaneous electrical signals and generates an analog ECG signal representative of the electrical activity of the patient's heart over time.

The circuitry 90 of the monitor recorder 14 also includes a flash memory 92, which the micro-controller 91 uses for storing ECG monitoring data and other physiology and information. The flash memory 92 also draws power externally from the battery provided on the electrode patch 15 via a pair of the electrical contacts 56. Data is stored in a serial flash memory circuit, which supports read, erase and program operations over a communications bus. The flash memory 92 enables the microcontroller 91 to store digitized ECG data. The communications bus further enables the flash memory 92 to be directly accessed externally over the external connector 95 when the monitor recorder 14 is interfaced to a download station.

The circuitry 90 of the monitor recorder 14 further includes an actigraphy sensor 94 implemented as a 3-axis accelerometer. The accelerometer may be configured to generate interrupt signals to the microcontroller 91 by independent initial wake up and free fall events, as well as by device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses, such as described in commonly-assigned U.S. Pat. No. 9,737,224, issued Aug. 22, 2017, the disclosure of which is incorporated by reference.

The microcontroller 91 includes an expansion port 98 that also utilizes the communications bus. External devices, separately drawing power externally from the battery provided on the electrode patch 15 or other source, can interface to the microcontroller 91 over the expansion port in half duplex mode. For instance, an external physiology sensor can be provided as part of the circuitry 90 of the monitor recorder 14, or can be provided on the electrode patch 15 with communication with the micro-controller 91 provided over one of the electrical contacts 56. The physiology sensor can include a $SpO_2$ sensor, blood pressure sensor, temperature sensor, respiratory rate sensor, glucose sensor, airflow sensor, volumetric pressure sensing, or other types of sensor or telemetric input sources. For instance, the integration of an airflow sensor is described in commonly-assigned U.S. Pat. No. 9,364,155, issued Jun. 14, 2016, the disclosure which is incorporated by reference. In a further embodiment, a wireless interface for interfacing with other wearable (or implantable) physiology monitors, as well as data offload and programming, can be provided as part of the circuitry 90 of the monitor recorder 14, or can be provided on the electrode patch 15 with communication with the microcontroller 91 provided over one of the electrical contacts 56, such as described in commonly-assigned U.S. Pat. No. 9,433,367, issued Sep. 6, 2016 the disclosure of which is incorporated by reference.

Finally, the circuitry 90 of the monitor recorder 14 includes patient-interfaceable components, including a tactile feedback button 96, which a patient can press to mark events or to perform other functions, and a buzzer 67, such as a speaker, magnetic resonator or piezoelectric buzzer. The buzzer 97 can be used by the microcontroller 91 to output feedback to a patient such as to confirm power up and initiation of ECG monitoring. Still other components as part of the circuitry 90 of the monitor recorder 14 are possible.

Figure 13:
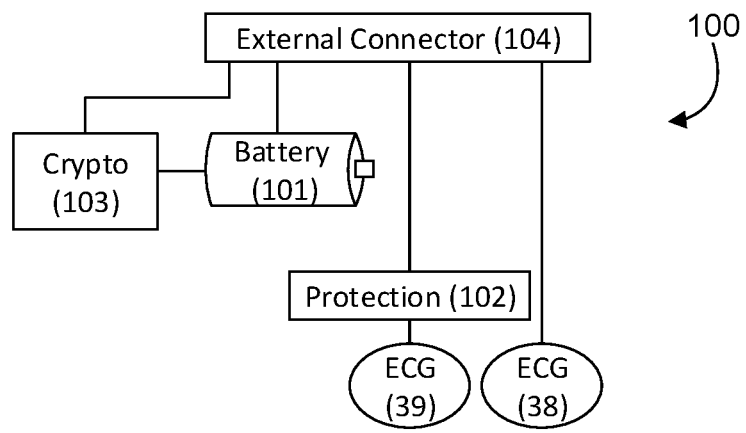
FIG. 13 is a functional block diagram showing the circuitry of the extended wear electrode patch of FIG. 4.

While the monitor recorder 14 operates under micro control, some of the electrical components of the electrode patch 15 operate passively, while others are active. FIG. 13 is a functional block diagram showing the circuitry 100 of the extended wear electrode patch 15 of FIG. 4. The circuitry 100 of the electrode patch 15 is electrically coupled with the circuitry 90 of the monitor recorder 14 through an external connector 104. The external connector 104 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 100 of the electrode patch 15 performs three primary functions. First, a battery 101 is provided in a battery compartment formed on the bottom surface of the non-conductive receptacle 25. The battery 101 is electrically interfaced to the circuitry 90 of the monitor recorder 14 as a source of external power. The unique provisioning of the battery 101 on the electrode patch 15 provides several advantages. First, the locating of the battery 101 physically on the electrode patch 15 lowers the center of gravity of the overall wearable monitor 12 and thereby helps to minimize shear forces and the effects of movements of the patient and clothing. Moreover, the housing 50 of the monitor recorder 14 is sealed against moisture and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Finally, the architecture of the monitor recorder 14 is open, in that other physiology sensors or components can be added by virtue of the expansion port of the microcontroller 91. Requiring those additional sensors or components to draw power from a source external to the monitor recorder 14 keeps power considerations independent of the monitor recorder 14. Thus, a battery of higher capacity could be introduced when needed to support the additional sensors or components without effecting the monitor recorders circuitry 90.

Second, the pair of ECG electrodes 38, 39 respectively provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 102, which is an inline resistor that protects the patient from excessive leakage current.

Last, in a further embodiment, the circuitry 100 of the electrode patch 15 includes a cryptographic circuit 103 to authenticate an electrode patch 15 for use with a monitor recorder 14. The cryptographic circuit 103 includes a device capable of secure authentication and validation. The cryptographic device 103 ensures that only genuine, non-expired, safe, and authenticated electrode patches 15 are permitted to provide monitoring data to a monitor recorder 14. Further, the cryptographic circuit can include readable and writeable memory for storing data received from the monitor recorder or external sensors, or providing instructions to the monitor recorder and external sensors, as further described below in detail below with reference to FIGS. 14 and 18. However, the readable and writeable memory for storing data can be provided separately from the cryptographic circuit.

Figure 14:
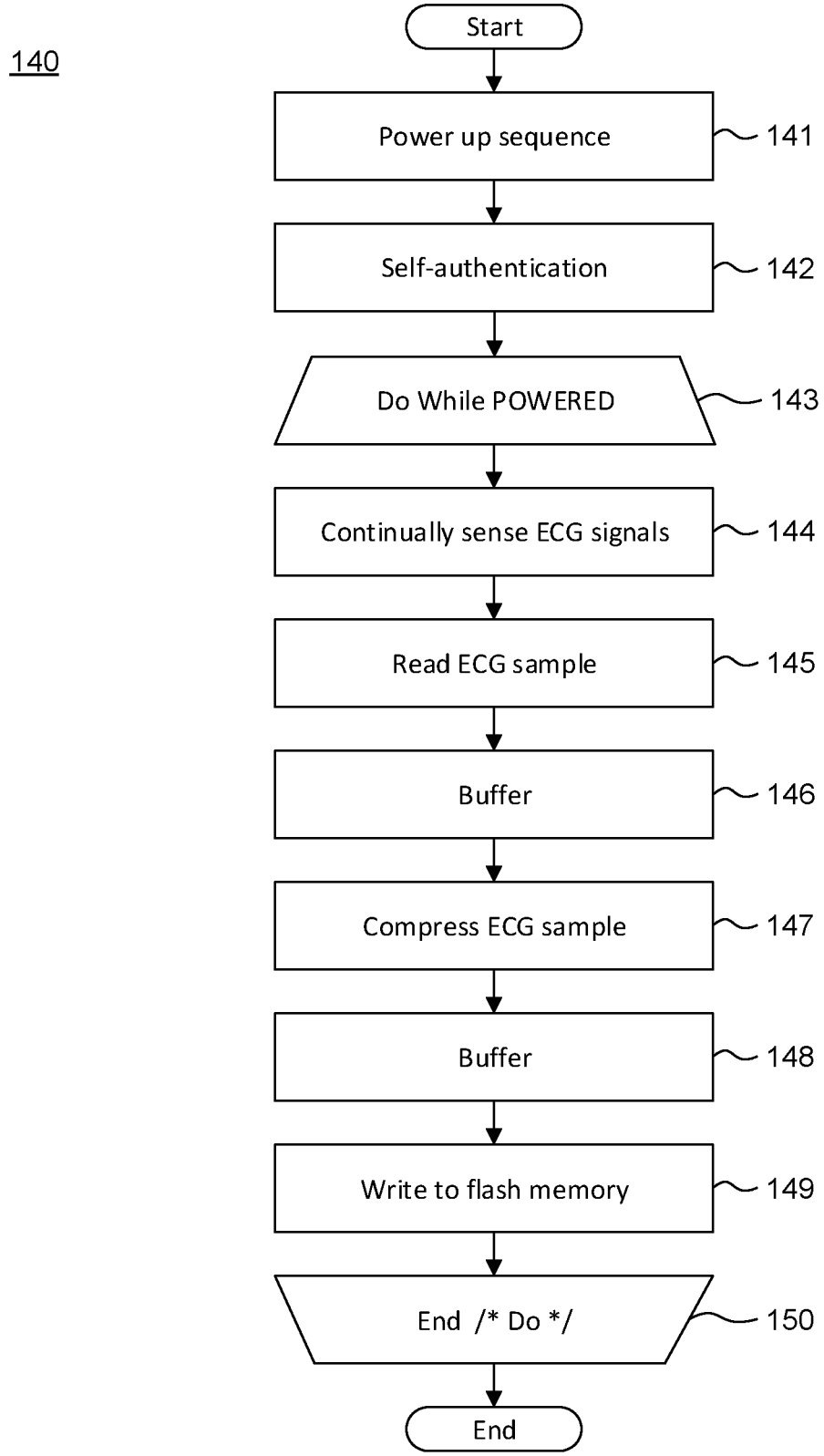
FIG. 14 is a flow diagram showing a monitor recorder-implemented method for monitoring ECG data for use in the monitor recorder of FIG. 4.

The monitor recorder 14 continuously monitors the patient's heart rate and physiology. FIG. 14 is a flow diagram showing a monitor recorder-implemented method 140 for monitoring ECG data for use in the monitor recorder 14 of FIG. 4. Initially, upon being connected to the set of pads 34 provided with the non-conductive receptacle 25 when the monitor recorder 14 is snapped into place, the microcontroller 91 executes a power up sequence (step 141) and performs self-authentication of the electrode patch 15 (step 142). During the power up sequence, the voltage of the battery 101 is checked, the state of the flash memory 92 is confirmed, both in terms of operability check and available capacity, and microcontroller operation is diagnostically confirmed.

Self-authentication is performed between the microcontroller 91 and the electrode patch 15 each time that the monitor recorder 14 is inserted into an electrode patch 15 (or other accessory) to ensure patient safety. An authenticated patch will conform to product quality standards, as well as applicable federal regulatory quality requirements and international standards, such as ISO 13485, IEC 60601-2-47 and IEC 60601-1. Quality assurance, through self-authentication, is crucial, as electrode patches 15 and other accessories may be authorized, but may not necessarily be manufactured, by the entity ultimately responsible for quality standards compliance. Self-authentication mitigates the risk of incorrect device output due to non-compliant accessories.

In one embodiment, the micro-controller 91 contains a private key or a precomputed digest, of which the electrode patch 15 (or other accessory) will have a copy. To authenticate an electrode patch 15 (or other accessory), the micro-controller 91 will challenge the electrode patch 15 (or other accessory) using a code hashed with the private key or precomputed digest. If the electrode patch 15 (or other accessory) responds correctly, the micro-controller 91 will continue with normal program execution. Otherwise, the monitor recorder 14 will signal an error condition, such as chirping the buzzer 97 to notify the patient. Failing self-authentication, other actions could also be taken.

In a further embodiment, an electrode patch 15 (or other accessory, such as a separate physiological sensor) can be set to operate for only a certain period of time. Upon authentication, the monitor recorder 14 will run with that electrode patch 15 (or other accessory) until the electrode patch 15 (or other accessory) is depleted. If the electrode patch 15 (or other accessory) is detected to be expired during self-authentication, the monitor recorder 14 will fail to operate or signal an error condition. To cause an electrode patch 15 (or other accessory) to expire after a certain amount of time has elapsed, the micro-controller 91 periodically writes into the read-only memory (ROM) of the cryptographic circuit 103. After the data in the ROM written by the micro-controller 91 has reached a certain fullness, the micro-controller 91 will turn off to ensure that an expired electrode patch 15 (or other accessory) does not create an unsafe condition, such as an incorrect output. Still other forms of authentication and device expiration are possible.

Figure 15:
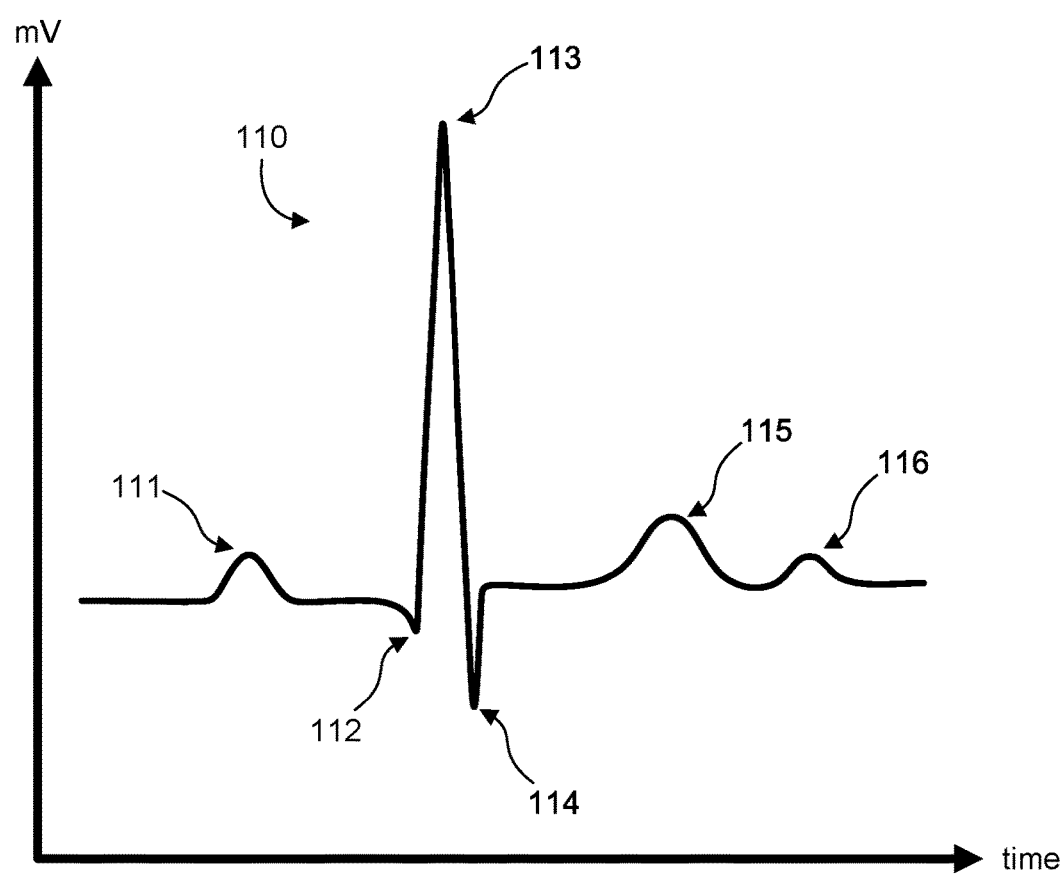
FIG. 15 is a graph showing, by way of example, a typical ECG waveform.

Following satisfactory completion of the power up sequence, an iterative processing loop (steps 143-150) is continually executed by the microcontroller 91. During each iteration (step 143) of the processing loop, the ECG frontend 93 (shown in FIG. 9) continually senses the cutaneous ECG electrical signals (step 144) via the ECG electrodes 38, 39 and is optimized to maintain the integrity of the P-wave. A sample of the ECG signal is read (step 145) by the micro-controller 91 by sampling the analog ECG signal output front end 93. FIG. 15 is a graph showing, by way of example, a typical ECG waveform 110. The x-axis represents time in approximate units of tenths of a second. The y-axis represents cutaneous electrical signal strength in approximate units of millivolts. The P-wave 111 has a smooth, normally upward, that is, positive, waveform that indicates atrial depolarization. The QRS complex usually begins with the downward deflection of a Q wave 112, followed by a larger upward deflection of an R-wave 113, and terminated with a downward waveform of the S wave 114, collectively representative of ventricular depolarization. The T wave 115 is normally a modest upward waveform, representative of ventricular depolarization, while the U wave 116, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the extended wear ambulatory electrocardiography and physiological sensor monitor described herein is medically unique and important. The long-term observation of these ECG indicia, as provided through extended wear of the wearable monitor 12, provides valuable insights to the patient's cardiac function and overall well-being.

Returning to the discussion with respect to FIG. 14, each sampled ECG signal, in quantized and digitized form, is temporarily staged in buffer (step 146), pending compression preparatory to storage in the flash memory 92 (step 147). Following compression, the compressed ECG digitized sample is again buffered (step 148), then written to the flash memory 92 (step 149) using the communications bus. Processing continues (step 150), so long as the monitoring recorder 14 remains connected to the electrode patch 15 (and storage space remains available in the flash memory 92), after which the processing loop is exited and execution terminates. Still other operations and steps are possible.

Figure 16:
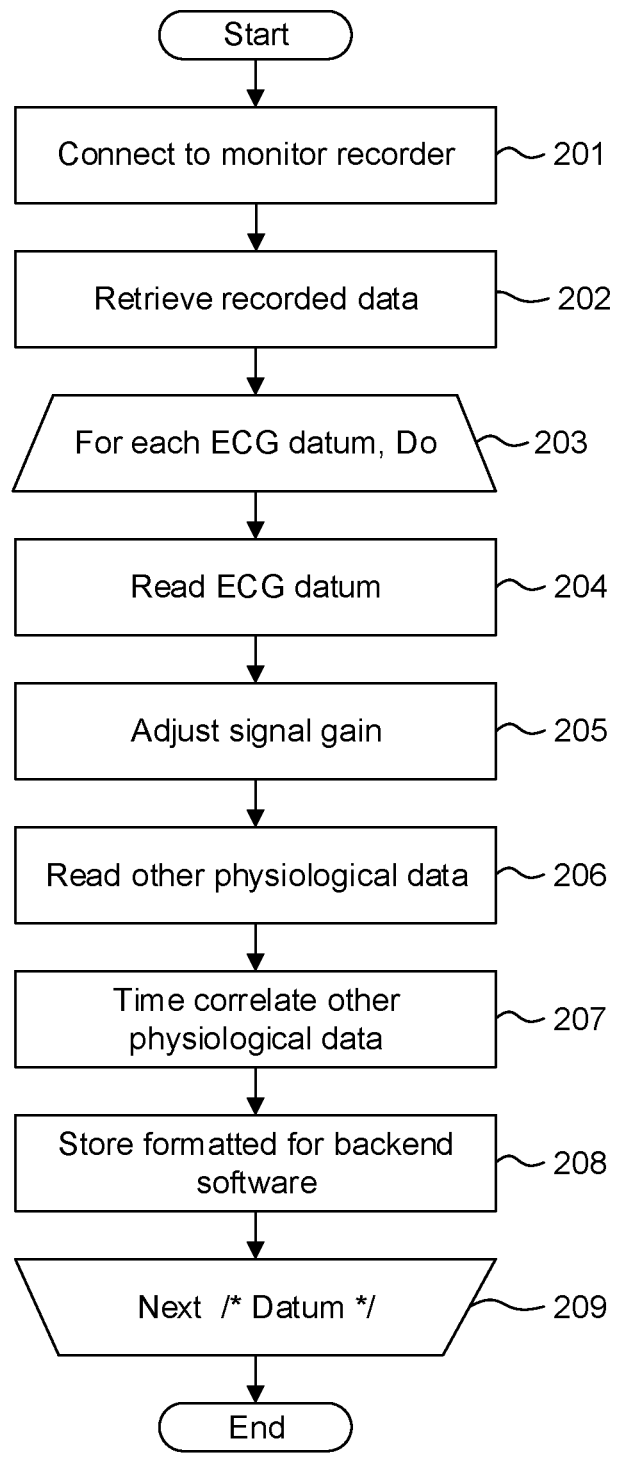
FIG. 16 is a flow diagram showing a method for offloading and converting ECG and other physiological data from an extended wear electrocardiography and physiological sensor monitor in accordance with one embodiment.

Once recorded, the ECG data can be offloaded and processed. FIG. 16 is a flow diagram showing a method 200 for offloading and converting ECG and other physiological data from an extended wear electrocardiography and physiological sensor monitor in accordance with one embodiment. The method 150 can be implemented in software and execution of the software can be performed on a download station 125, which could be a programmer or other device, or a computer system, including a server 122 or personal computer 129, such as further described supra with reference to FIG. 3, as a series of process or method modules or steps. For convenience, the method 200 will be described in the context of being performed by a personal computer 136 or other connectable computing device (shown in FIG. 3) as middleware that converts ECG data and other information into a format suitable for use by a third-party post-monitoring analysis program. Execution of the method 200 by a computer system would be analogous mutatis mutandis.

Initially, the download station 125 is connected to the monitor recorder 14 (step 201), such as by physically interfacing to a set of terminals 128 on a paired receptacle 127 or by wireless connection, if available. The data stored on the monitor recorder 14, including ECG and physiological monitoring data, other recorded data, and other information are retrieved (step 202) over a hard link 135 using a control program 137 ("Ctl") or analogous application executing on a personal computer 136 or other connectable computing device.

The data retrieved from the monitor recorder 14 is in a proprietary storage format and each datum of recorded ECG monitoring data, as well as any other physiological data or other information, must be converted, so that the data can be used by a third-party post-monitoring analysis program. Each datum of ECG monitoring data is converted by the middleware (steps 203-209) in an iterative processing loop. During each iteration (step 203), the ECG datum is read (step 204) and, if necessary, the gain of the ECG signal is adjusted (step 205) to compensate, for instance, for relocation or replacement of the electrode patch 15 during the monitoring period.

In addition, depending upon the configuration of the wearable monitor 12, other physiological data (or other information), including patient events, such as a fall, peak activity level, detection of patient activity levels and states, sedentary detection and so on, may be recorded along with the ECG monitoring data. For instance, actigraphy data may have been sampled by the actigraphy sensor 94 based on a sensed event occurrence, such as a sudden change in orientation due to the patient taking a fall. In response, the monitor recorder 14 will embed the actigraphy data samples into the stream of data, including ECG monitoring data that is recorded to the flash memory 92 by the micro-controller 91. Post-monitoring, the actigraphy data is temporally matched to the ECG data to provide the proper physiological context to the sensed event occurrence. As a result, the three-axis actigraphy signal is turned into an actionable event occurrence that is provided, through conversion by the middleware, to third party post-monitoring analysis programs, along with the ECG recordings contemporaneous to the event occurrence. Other types of processing of the other physiological data (or other information) are possible.

Thus, during execution of the middleware, any other physiological data (or other information) that has been embedded into the recorded ECG monitoring data is read (step 206) and time-correlated to the time frame of the ECG signals that occurred at the time that the other physiological data (or other information) was noted (step 207). Finally, the ECG datum, signal gain adjusted, if appropriate, and other physiological data, if applicable and as time-correlated, are stored in a format suitable to the backend software (step 208) used in post-monitoring analysis. Processing continues (step 209) for each remaining ECG datum, after which the processing loop is exited and execution terminates.

Figure 17:
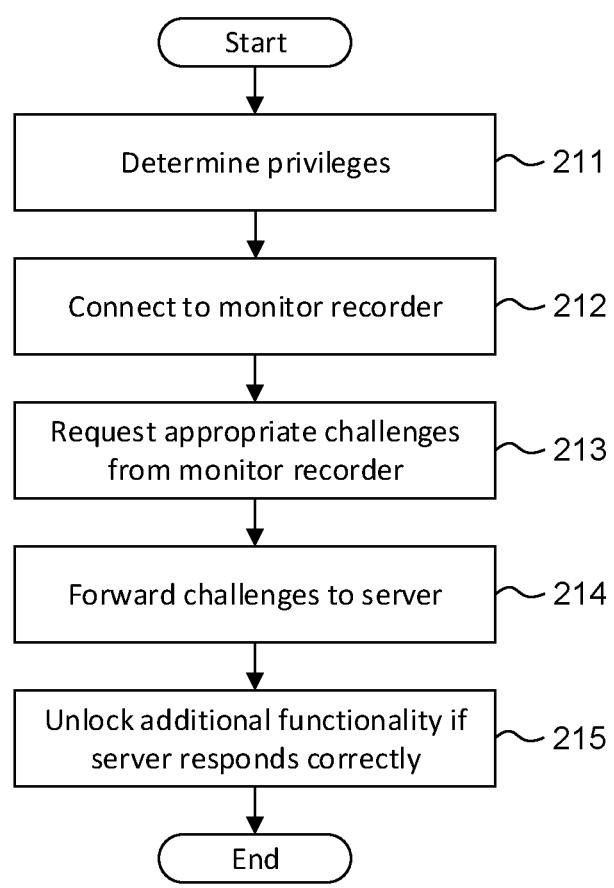
FIG. 17 is a flow diagram showing a method for providing a self-authenticating electrocardiography monitoring circuit in accordance with one embodiment.

Additionally, in one embodiment, the patient management program 123 could manage a subscription service that authorizes a monitor recorder 14 to operate for a set period of time or under pre-defined operational parameters and privileges. FIG. 17 is a flow diagram showing a method 210 for providing a self-authenticating electrocardiography monitoring circuit in accordance with one embodiment. The method 210 can be implemented in software and execution of the software can be performed on a download station 125, which could be a programmer or other device, or a computer system, including a server 122 or personal computer 129, such as further described supra with reference to FIG. 3, as a series of process or method modules or steps. For convenience, the method 210 will be described in the context of being performed by a download station 125. Execution of the method 210 by a computer system would be analogous mutatis mutandis.

In terms of a subscription business model, devices, such as the monitor recorder 14, could be sold at low cost, and a patient would only need to pay a monitoring service provider when they want to use their device. The subscription service could be implemented by the server 122 or other comparable computer system, which would provide a user interface to patients through which they could select and purchase desired additional functionality. A patient is able to "reload" their device with more time or pre-defined operational parameters and privileges using a challenge response authentication scheme through a download station 125. Initially, the patient determines what pre-defined operational parameters or privileges he wishes to purchase (step 211), such as running time, number of uses, monitoring features, and so on, and the patient's selections are provided to the server 122 using, for instance, a personal computer 129, or similar device. The download station 125 connects to the monitor recorder 14 (step 212), such as by physically interfacing to a set of terminals 128 on a paired receptacle 127 or by wireless connection, if available. The download station 125 communicate with the monitor recorder 14 and requests appropriate challenges (step 213), which are forwarded to the patient management program 123 executing on the server 122. Upon receiving (step 214) the forwarded challenges, the monitor recorder 14 will only unlock the requested additional functionality if the server 122 responds correctly (step 215). Thus, the server 122 can preclude authorizing the additional functionality by providing an incorrect response. Other types of pre-defined operational parameter and privilege authorization schemes are possible.

Figure 18:
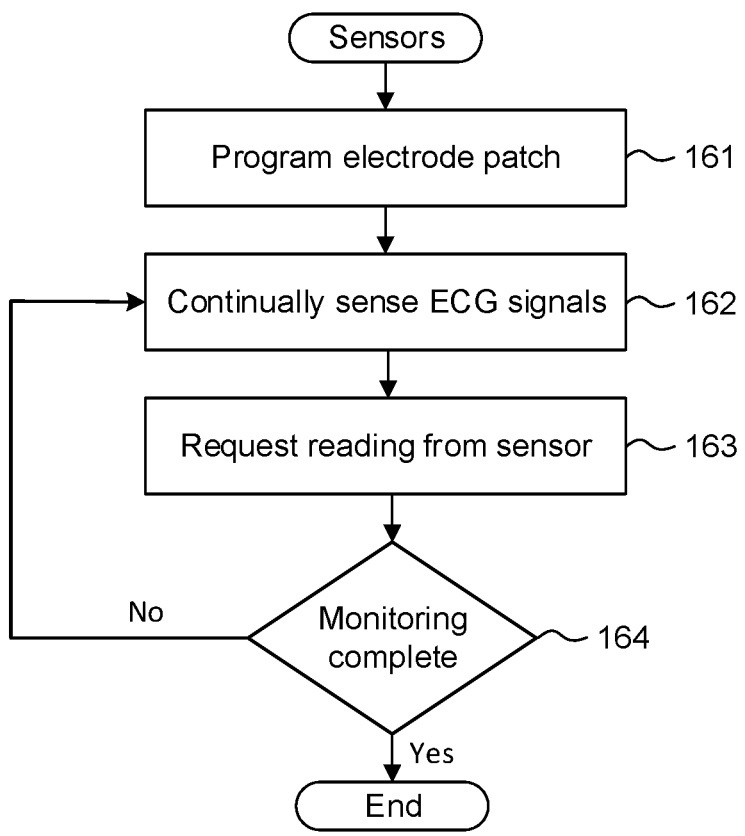
FIG. 18 is a flow diagram showing, by way of example, a process for obtaining physiological data from a physiological sensor.

In a further embodiment, physiological data can be collected via one or more physiological sensors, such as a $SpO_2$ sensor, blood pressure sensor, temperature sensor, respiratory rate sensor, glucose sensor, airflow sensor, volumetric pressure sensing, or other types of sensor or telemetric input sources continually or on demand as instructed by the electrode patch. Generally, continually obtaining physiological data from some types of sensors, such as a high resolution temperature sensor is not optimal nor preferred due to the large amounts of processing and memory required to obtain and store the data. However, sampling of the data randomly or at predetermined times as instructed by the electrode patch makes obtaining such data possible using the extended wear device, such as the electrocardiography and physiological sensor monitor. FIG. 18 is a flow diagram showing, by way of example, a process 160 for obtaining physiological data from a physiological sensor. Memory provided on the electrode patch is programmed (step 161) to enable and disable features, including obtaining physiological measurements via at least one physiological sensor at different times over a period of time. In one embodiment, the authentication or crypto circuit 103 (shown in FIG. 13) on the electrode patch includes programmable read and write memory space. However, in a different embodiment, the programmable read and write memory is provided separate from the crypto circuit. In one example, the programmed features can include predetermined times or a request for random times at which data is to be obtained via a physiological monitor. Other programmable features are also possible.

Once the monitor is applied to a patient and the electrode patch is authenticated by the monitor recorder, the electrocardiography and physiological sensor monitor continually senses (step 162) ECG signals upon authentication until the electrode patch is determined to be expired or is otherwise terminated. Meanwhile, the electrode patch can request (step 163) readings of physiological data from one or more physiological sensors provided as part of the circuitry of the monitor recorder or provided on the electrode patch. Alternatively or in addition, the physiological data can be wirelessly connected or external to the electrocardiography and physiological sensor monitor. When provided on the electrode patch, the physiological sensor can communicate with the micro-controller of the monitor recorder via one or more of the electrical contacts to obtain and store the received physiological data.

The request for data from the electrode patch can be provided based on a set of sampling instructions preprogrammed on the electrode patch, including instructions to request the physiological data randomly or at predetermined times, as described above. Other types and kinds of instructions are possible for sampling, such as requesting a reading from one or more of the physiological sensors when the patient presses the patient tactile feedback button (shown in FIG. 4) to mark events, such as a cardiac episode, when a user is out of breath or feels his heart racing. The electrode patch can be preprogrammed at the time of manufacture, or after manufacture and prior to distribution to a patient. Based on the data request, the physiological sensor for which the request was directed, obtains a reading of the corresponding physiological data, which is then provided to the monitor recorder for storage and later downloading via a download station with the ECG data.

During monitoring of the ECG signals and physiological data, a determination is made as to whether all monitoring is complete (step 164). For example, monitoring can be complete when the electrode patch expires, such as based on an amount of data obtained or recorded, a new electrode patch should replace the current electrode patch, or a predetermined time for monitoring has been reached, such as described in commonly-assigned U.S. patent application Ser. No. 16/208,450, filed Dec. 3, 2018, pending, the disclosure of which is incorporated by reference. If monitoring is complete, no further ECG signals or physiological data are recorded. However, if not complete, the ECG signals are continually recorded (step 162), while the physiological data is obtained (step 163) according to instructions from the electrode patch.

In one embodiment, different types of physiological sensors can be incorporated into the electrode patch 15 for use with the monitor recorder 14 as custom electrode patches. Specifically, each electrode patch can include a different physiological sensor and the electrode patches can be interchanged to work with the monitor recorder to obtain different types of physiological data. When instructed, the electrode patch requests a reading from the physiological sensor according to programmed timing. Alternatively, the physiological sensors are provided as part of the circuitry of the monitor recorder and each electrode patch is programmed to provide sampling instructions from the physiological sensor. For instance, some physiological data should be collected more frequently than other types of physiological data. In a further embodiment, the electrode patch 15 can store sampling instructions for more than one physiological sensor at a time.

In one example, a high resolution temperature sensor can be provided on the electrode patch or as part of the circuitry of the monitor recorder to take temperature measures at a high sample rate. Instructions from the electrode patch, which have been preprogrammed, instruct the high resolution temperature sensor when to begin measuring temperature and when to stop measuring the temperature, as well as how many times the temperature should be measured over a time period, which allows the electrocardiography and physiological sensor monitor to obtain the data and also continually monitor the ECG signals over time without utilizing large amounts of processing power and memory of the monitor. The instructions can also include a duration of measurement, which can be the same or different for each obtained data measurement.

In a further embodiment, multiple patches, each programmed for a different physiological sensor or with different sampling rates for the same physiological sensor can be used with the same monitor recorder.

While the invention has been particularly shown and described as referenced to the embodiments thereof, those skilled in the art will understand that the foregoing and other changes in form and detail may be made therein without departing from the spirit and scope.

What is claimed is:

1. An electrocardiography monitoring system, comprising:
    a flexible backing formed of an elongated strip of stretchable material;
    an electrocardiographic electrode respectively affixed to and conductively exposed on a contact surface of each end of the elongated strip;
    a flexible circuit affixed on each end to the elongated strip and comprising a pair of circuit traces each originating within one of the ends of the elongated strip and electrically coupled to one of the electrocardiographic electrodes;
    a non-conductive receptacle securely adhered on one of the ends of the elongated strip on a surface opposite the contact surface and formed to removably receive an electrocardiography monitor operable to obtain electrocardiographic signals through the electrocardiographic electrodes, wherein the non-conductive receptacle comprises electrode terminals aligned to electrically interface the pair of circuit traces to the electrocardiography monitor;
    a crypto circuit comprising memory on the flexible backing; and
    a battery to provide power to at least one physiological sensor provided with the electrocardiography monitor or on the flexible backing to obtain readings of physiological data, wherein the battery is positioned on one end of the flexible backing underneath the non-conductive receptacle and the electrocardiography monitor when received by the non-conductive receptacle and further wherein the flexible backing reduces shear forces by comprising a low center of gravity.

2. A system according to claim 1, further comprising:
    the electrocardiography monitor; and
    a download station to retrieve the electrocardiographic signals from the electrocardiography monitor.

3. A system according to claim 2, wherein the electrocardiographic signals are converted into a different format via middlewear on the download station.

4. A system according to claim 3, wherein the electrocardiographic signals are retrieved from the download station by a server that remotely interfaces with the download station.

5. A system according to claim 1, wherein the physiological sensor comprises one of a SpO2 sensor, blood pressure sensor, temperature sensor, respiratory rate sensor, glucose sensor, airflow sensor, or volumetric pressure sensor.

6. A system according to claim 1, further comprising:
    the electrocardiography monitor, comprising:
        a sealed housing adapted to be removably secured into the non-conductive receptacle; and
        electronic circuitry comprised within the sealed housing, comprising:
            an electrocardiographic front end circuit configured to sense the electrocardiographic signals through the electrocardiographic electrodes provided on the flexible backing; and
            flash memory to record the electrocardiographic signals.

7. A system according to claim 6, wherein the electronic circuitry of the electrocardiography monitor is configured to embed the physiological data into a stream of the electrocardiographic signals.

8. A system to claim 6, wherein the electronic circuitry of the electrocardiography monitor is configured to match the electrocardiographic signals to the physiological data.

9. An electrocardiography monitoring system according to claim 1, wherein the memory is programed with a sampling rate for the physiological sensor to obtain the readings of physiological data.

10. A system according to claim 9, wherein the physiological sensor is configured to record the physiological data based on the sampling rate.

11. An extended wear electrocardiography and physiological sensor monitor, comprising:
    an electrocardiography monitor, comprising:
        a sealed housing; and
        electronic circuitry comprised within the sealed housing, comprising:

an externally-powered micro-controller; and
an electrocardiographic front end circuit electrically interfaced to the micro-controller and operable to sense electrocardiographic signals; and
an electrocardiography patch, comprising:
a flexible backing formed of an elongated strip of stretchable material;
an electrocardiographic electrode affixed to and conductively exposed on a contact surface of each end of the elongated strip;
a flexible circuit affixed on each end to the elongated strip and comprising a pair of circuit traces each originating within one of the ends of the elongated strip and electrically coupled to one of the electrocardiographic electrodes;
a non-conductive receptacle securely adhered on one of the ends of the elongated strip opposite the contact surface and formed to removably receive the electrocardiography monitor, the non-conductive receptacle comprising electrode terminals aligned to electrically interface the pair of circuit traces to the electrocardiography monitor;
a crypto circuit comprising memory on the flexible backing; and
a battery to provide power to at least one physiological sensor provided with the electrocardiography monitor or on the flexible backing to obtain readings of physiological data, wherein the physiological sensor is electrically interfaced with the micro-controller over an expansion bus and the battery is positioned on one end of the flexible backing underneath the non-conductive receptacle and the electrocardiography monitor when received by the non-conductive receptacle and further wherein the electrocardiography patch reduces shear forces by comprising a low center of gravity.

12. An extended wear electrocardiography and physiological sensor monitor according to claim 11, further comprising:
a download station to retrieve the electrocardiographic signals from the from the electrocardiography monitor.

13. An extended wear electrocardiography and physiological sensor monitor according to claim 12, wherein the electrocardiographic signals are converted into a different format via middlewear on the download station.

14. An extended wear electrocardiography and physiological sensor monitor according to claim 13, further comprising:
a server to remotely interface with the download station and configured to retrieve the differently formatted electrocardiographic signals.

15. An extended wear electrocardiography and physiological sensor monitor according to claim 11, wherein each physiological sensor comprises one of a SpO2 sensor, blood pressure sensor, temperature sensor, respiratory rate sensor, glucose sensor, airflow sensor, or volumetric pressure sensor.

16. An extended wear electrocardiography and physiological sensor monitor according to claim 11, wherein the electronic circuitry is configured to embed the physiological data into a stream of the electrocardiographic signals.

17. An extended wear electrocardiography and physiological sensor monitor according to claim 11, wherein the electronic circuitry is configured to match the physiological data to the electrocardiographic signals.

18. An extended wear electrocardiography and physiological sensor monitor according to claim 11, wherein the memory is programed with a sampling rate for the physiological sensor to obtain the readings of physiological data and samples of the physiological data are stored in a flash memory of the electrocardiography monitor operable through the expansion bus.

19. An extended wear electrocardiography and physiological sensor monitor according to claim 18, further comprising:
at least one other electrocardiography patch with a flexible backing electrocardiography electrodes, flexible circuit, non-conductive receptacle, crypto circuit and battery to replace the electrocardiography patch, wherein each electrocardiography patch comprises memory with a different sampling rate for different physiological data stored in the memory.

20. An extended wear electrocardiography and physiological sensor monitor according to claim 18, wherein the physiological sensor is configured to record the physiological data based on the sampling rate.

* * * * *